(12) United States Patent
Shmarev et al.

(10) Patent No.: US 8,107,173 B2
(45) Date of Patent: *Jan. 31, 2012

(54) CATADIOPTRIC OPTICAL SYSTEM FOR SCATTEROMETRY

(75) Inventors: Yevgeniy Konstanitinovich Shmarev, Lagrangeville, NY (US); Stanislav Y. Smirnov, Bethel, CT (US); Irina I. Pozhinskaya, Fairfield, CT (US)

(73) Assignee: ASML Holding N.V., Veldhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/608,654

(22) Filed: Oct. 29, 2009

(65) Prior Publication Data
US 2010/0046092 A1  Feb. 25, 2010

Related U.S. Application Data

(63) Continuation of application No. 11/779,691, filed on Jul. 18, 2007, now Pat. No. 7,633,689.

(51) Int. Cl.
*G02B 17/00* (2006.01)
*G02B 21/00* (2006.01)
*G02B 23/00* (2006.01)

(52) U.S. Cl. .................. 359/726; 359/364

(58) Field of Classification Search .......... 359/726–731, 359/364–366
See application file for complete search history.

(56) References Cited

U.S. PATENT DOCUMENTS

| | | |
|---|---|---|
| 2,380,887 A | 7/1945 | Warnisham |
| 2,683,394 A | 7/1954 | Polanyi et al. |
| 3,825,322 A | 7/1974 | Mast |
| 4,757,354 A | 7/1988 | Sato et al. |
| 5,136,413 A | 8/1992 | MacDonald et al. |
| 5,175,591 A | 12/1992 | Dunn et al. |
| 5,347,364 A | 9/1994 | Kawasaki et al. |
| 5,793,538 A | 8/1998 | Cameron et al. |
| 5,912,741 A | 6/1999 | Carter et al. |
| 6,235,624 B1 | 5/2001 | Sasaki et al. |
| 6,256,154 B1 | 7/2001 | Kubota et al. |
| 6,430,139 B1 | 8/2002 | Yoo et al. |
| 6,473,243 B1 | 10/2002 | Omura |
| 6,493,156 B1 | 12/2002 | Oh et al. |

(Continued)

FOREIGN PATENT DOCUMENTS

EP  0 243 950 A2  11/1987

(Continued)

OTHER PUBLICATIONS

Extended Search Report for European Application No. 08252443.0-2217/2017662 mailed Mar. 25, 2009, 9 pgs.

(Continued)

*Primary Examiner* — Alicia M Harrington
(74) *Attorney, Agent, or Firm* — Sterne, Kessler, Goldstein & Fox P.L.L.C.

(57) ABSTRACT

A catadioptric optical system having a high numerical aperture operates in a wide spectral range. The catadioptric system includes a correcting plate and an optical system. The correcting plate conditions electromagnetic radiation to correct at least one aberration. The optical system reflects a first portion of the conditioned electromagnetic radiation, refracts a second portion of the conditioned electromagnetic radiation, and focuses the reflected first portion of the conditioned electromagnetic radiation onto a target portion of a substrate. The first portion of the electromagnetic radiation is not refracted by an optical element, allowing the catadioptric optical system to operate in a broad spectral range.

12 Claims, 12 Drawing Sheets

U.S. PATENT DOCUMENTS

| | | |
|---|---|---|
| 6,560,039 B1 | 5/2003 | Webb et al. |
| 6,785,051 B2 | 8/2004 | Allan et al. |
| 6,938,890 B2 | 9/2005 | Yoo et al. |
| 6,940,803 B2 | 9/2005 | Hatano |
| 6,956,694 B2 | 10/2005 | Shafer et al. |
| 7,075,721 B2 | 7/2006 | Webb et al. |
| 7,564,633 B2 | 7/2009 | Webb |
| 7,633,689 B2 * | 12/2009 | Shmarev et al. ............... 359/726 |
| 2006/0033921 A1 | 2/2006 | Den Boef et al. |
| 2006/0109436 A1 | 5/2006 | Van Der Laan et al. |
| 2006/0219930 A1 | 10/2006 | Lange |
| 2006/0238856 A1 | 10/2006 | Shafer et al. |
| 2006/0279837 A1 | 12/2006 | Chuang et al. |

FOREIGN PATENT DOCUMENTS

| | | |
|---|---|---|
| JP | 48-078954 | 10/1973 |
| JP | 63-014112 A | 1/1988 |
| JP | 07-012717 A | 1/1995 |
| JP | 09-068604 A | 3/1997 |
| JP | 10-013159 A | 1/1998 |
| JP | 2000-206411 | 7/2000 |
| JP | 2001-021704 A | 1/2001 |
| JP | 2001-133689 A | 5/2001 |
| JP | 2001-176118 A | 6/2001 |
| JP | 2001-194582 A | 7/2001 |
| JP | 3211985 B2 | 7/2001 |
| JP | 3402934 B2 | 2/2003 |
| JP | 2003-161886 A | 6/2003 |
| JP | 2004-536454 A | 12/2004 |
| JP | 2005-530333 A | 10/2005 |
| JP | 2007-514179 A | 5/2007 |
| JP | 2007-523383 A | 8/2007 |
| JP | 2007-531060 A | 11/2007 |
| WO | WO 00/08642 A1 | 2/2000 |
| WO | WO 00/39623 A1 | 7/2000 |
| WO | WO 02/50509 A2 | 6/2002 |
| WO | WO 2006/059330 A2 | 6/2006 |

OTHER PUBLICATIONS

Non-Final Rejection mailed Sep. 10, 2008 for U.S. Appl. No. 11/779,691, 9 pgs.

Second Non-Final Rejection mailed Mar. 4, 2009 for U.S. Appl. No. 11/779,691, 8 pgs.

Notice of Allowance mailed Aug. 11, 2009 for U.S. Appl. No. 11/779,691, 6 pgs.

English language Abstract of Japanese Patent Publication No. 63-014112 A, Published Jan. 21, 1988, Japanese Patent Office (listed on the accompanying PTO/SB/08A form as document FP2); 2 pages.

English language Abstract of Japanese Patent Publication No. 07-012717 A, Published Jan. 17, 1995, Japanese Patent Office (listed on the accompanying PTO/SB/08A form as document FP3); 1 page.

English language Abstract of Japanese Patent Publication No. 09-068604 A, Published Mar. 11, 1997, Japanese Patent Office (listed on the accompanying PTO/SB/08A form as document FP4); 1 page.

English language Abstract of Japanese Patent Publication No. 10-013159 A, Published Jan. 16, 1998, Japanese Patent Office (listed on the accompanying PTO/SB/08A form as document FP5); 1 page.

English language Abstract of Japanese Patent Publication No. 2000-206411 A, Published Jul. 28, 2000, Japanese Patent Office (listed on the accompanying PTO/SB/08A form as document FP8); 1 page.

English language Abstract of Japanese Patent Publication No. 2001-021704 A, Published Jan. 26, 2001, Japanese Patent Office (listed on the accompanying PTO/SB/08A form as document FP9); 2 pages.

English language Abstract of Japanese Patent Publication No. 2001-133689 A, Published May 18, 2001, Japanese Patent Office (listed on the accompanying PTO/SB/08A form as document FP10); 2 pages.

English language Abstract of Japanese Patent Publication No. 2001-176118 A, Published Jun. 29, 2001, Japanese Patent Office (listed on the accompanying PTO/SB/08A form as document FP11); 1 page.

English language Abstract of Japanese Patent Publication No. 2001-194582 A, Published Jul. 19, 2001, Japanese Patent Office (listed on the accompanying PTO/SB/08A form as document FP12); 2 pages.

English language Abstract of Japanese Patent Publication No. 2003-161886 A, Published Jun. 6, 2003, Japanese Patent Office (listed on the accompanying PTO/SB/08A form as document FP15); 1 page.

English translation of Japanese Notice of Reasons for Rejection mailed Feb. 7, 2011, directed to related Japanese Patent Application No. 2008-180850; 5 pages.

* cited by examiner

CATADIOPTRIC OPTICAL SYSTEM FOR SCATTEROMETRY

CROSS-REFERENCE TO RELATED APPLICATIONS

This application is a continuation of U.S. Non-Provisional application Ser. No. 11/779,691, filed Jul. 18, 2007 (now U.S. Pat. No. 7,633,689, issued Dec. 15, 2009), which is incorporated by reference herein in its entirety.

BACKGROUND

1. Field of the Invention

The present invention is generally directed to optical systems, and more particularly to catadioptric optical systems.

2. Related Art

A lithographic apparatus is a machine that applies a desired pattern onto a substrate or part of a substrate. A lithographic apparatus can be used, for example, in the manufacture of flat panel displays, integrated circuits (ICs) and other devices involving fine structures. In a conventional apparatus, a patterning device, which can be referred to as a mask or a reticle, can be used to generate a circuit pattern corresponding to an individual layer of an IC, flat panel display, or other device. This pattern can be transferred onto all or part of the substrate (e.g., a glass plate, a wafer, etc.), by imaging onto a layer of radiation-sensitive material (e.g., resist) provided on the substrate.

The patterning device can be used to generate, for example, an IC pattern. The patterning device can additionally or alternatively be used to generate other patterns, for example a color filter pattern or a matrix of dots. Instead of a mask, the patterning device can be a patterning array that comprises an array of individually controllable elements. The pattern can be changed more quickly and for less cost in such a system compared to a mask-based system.

After patterning the substrate, measurements and inspection are typically performed. The measurement and inspection step typically serves two purposes. First, it is desirable to detect any target areas where the pattern in the developed resist is faulty. If a sufficient number of target areas are faulty, the substrate can be stripped of the patterned resist and re-exposed, hopefully correctly, rather than making the fault permanent by carrying out a process step, e.g., an etch, with a faulty pattern. Second, the measurements may allow errors in the lithographic apparatus, e.g., illumination settings or exposure dose, to be detected and corrected for in subsequent exposures.

However, many errors in the lithographic apparatus cannot easily be detected or quantified from the patterns printed in resist. Detection of a fault does not always lead directly to its cause. Thus, a variety of off-line procedures (i.e., procedures carried out in addition to normal processing of the substrate) for detecting and measuring errors in the lithographic apparatus are known. These may involve replacing the substrate with a measuring device or carrying out exposures of special test patterns, e.g., at a variety of different machine settings. Such off-line techniques take time, often a considerable amount, reducing production time and during which the end products of the apparatus will be of an unknown quality until the measurement results are made available.

In-line measurement and inspection procedures (i.e., procedures carried out during the normal processing of the substrate) are known. For example, scatterometry is an optical metrology technique that can be used for in-line measurements of critical dimension (CD) and overlay. There are two main scatterometry techniques:

(1) Spectroscopic scatterometry measures the properties of scattered light at a fixed angle as a function of wavelength, usually using a broadband light source, such as xenon, deuterium, or halogen based light source such as a xenon arc lamp. The fixed angle can be normally incident or obliquely incident.

(2) Angle-resolved scatterometry measures the properties of scattered light at a fixed wavelength as a function of angle of incidence, usually using a laser as a single wavelength light source.

Using scatterometry the structure giving rise to a reflected spectrum is reconstructed, e.g., using real-time regression or by comparison to a library of patterns derived by simulation. Reconstruction involves minimization of a cost function. Both approaches calculate the scattering of light by periodic structures. The most common technique is Rigorous Coupled-Wave Analysis (RCWA), though light scattering can also be calculated by other techniques, such as Finite Difference Time Domain (FDTD) or Integral Equation techniques.

Known scatterometers, however, have several drawbacks. For example, conventional scatterometers only detect one wavelength at a time. As a result, spectra with more than one wavelength have to be time-multiplexed, which increases the total acquisition time taken to detect and process the spectra.

Given the foregoing, what is needed is an apparatus that can be used for in-line measuring and inspection in a lithographic apparatus.

SUMMARY

According to one embodiment of the present invention, there is provided a catadioptric system comprising a correcting plate and an optical system. The correcting plate is configured to condition electromagnetic radiation to correct at least one aberration. The optical system is configured to reflect a first portion of the conditioned electromagnetic radiation, to refract a second portion of the conditioned electromagnetic radiation, and to focus the reflected first portion of the conditioned electromagnetic radiation onto a target portion of a substrate. The first portion of the electromagnetic radiation is not refracted by an optical element, allowing the catadioptric optical system to operate in a broad spectral range.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIGS. 1 and 2 depict lithographic projection apparatus according to embodiments of the present invention.

FIGS. 3A-C depict an example scatterometer.

Figure 1:
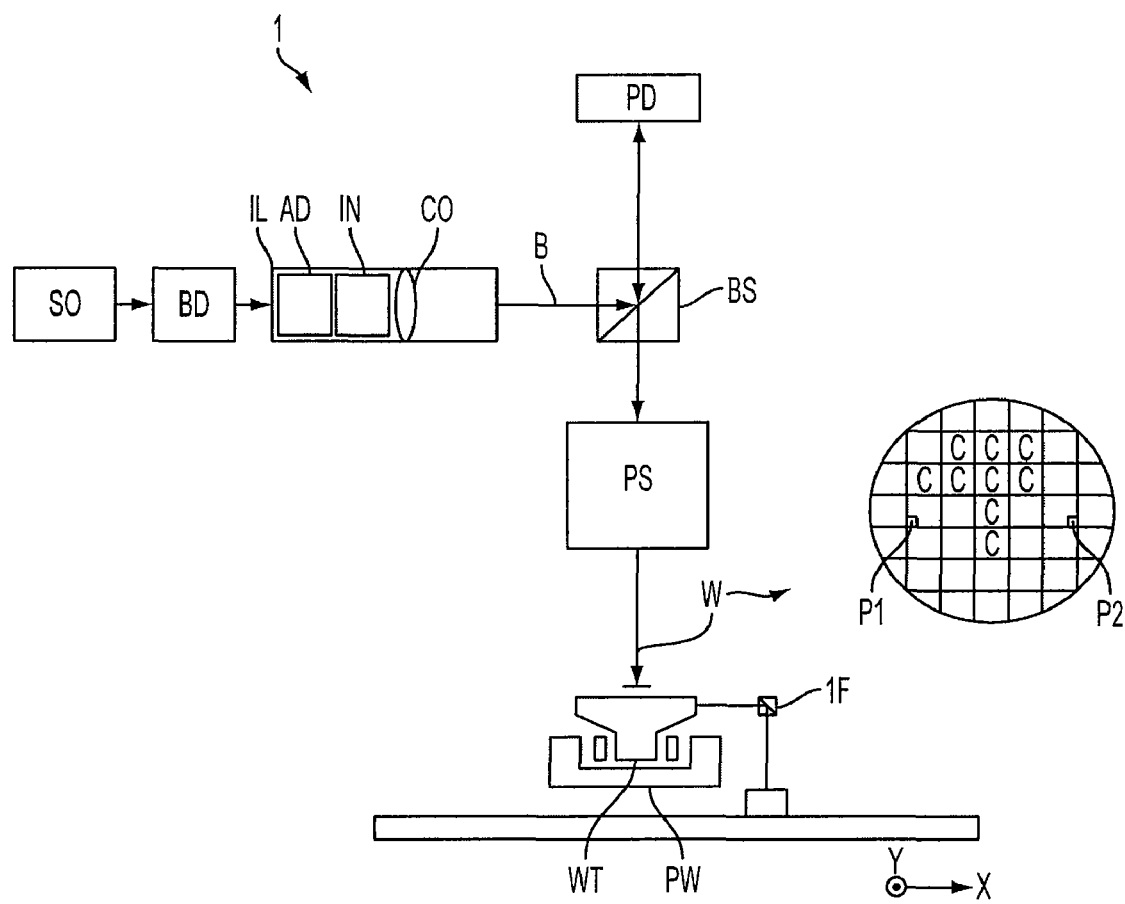

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Introduction

The present invention provides a catadioptric optical system for scatterometry. In the specification, reference to "one embodiment", "an embodiment", "an example embodiment", etc., indicates that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

A catadioptric optical system in accordance with an embodiment of the present invention includes (i) a mirror system to provide a high numerical aperture and achromatism, and (ii) a nearly afocal refractive element to correct one or more aberrations (such as coma). The catadioptric optical system can be used as a special objective in a UV-visible scatterometer for critical dimension (CD) and overlay measurements (as depicted, for example, in FIG. 4).

The special objective can be embedded in a system that includes both an alignment branch and a sensing branch. In such an embodiment, the alignment branch includes refractive elements that are embedded in the optical design of the sensing branch. The refractive elements are situated in a volume that is obscured by a small spherical mirror. A first surface (or group of surfaces) in the alignment branch has a common surface (or surfaces) with a convex reflective surface in the sensing branch. The convex reflective surface can be partly reflective (such as, for example, 80% reflection) or have a spectral-dependent reflection that provides light distribution between the sensing and alignment branches. Alternatively, the special objective can be used in a system that only includes a sensing branch.

A catadioptric optical system in accordance with a scatterometer of one or more embodiments of the present invention can have several desirable characteristics over conventional scatterometers. For example, such a catadioptric optical system has a very high numerical aperture (such as, for example, approximately 0.95) and operates in a wide spectral range (such as, for example, approximately 200 nanometers to 1000 nanometers). In addition, such a catadioptric optical system produces low obscuration in the sensing branch (approximately 14%) and no obscuration in the alignment branch. Moreover, such a catadioptric optical system includes fewer optical surfaces in the sensing branch compared to conventional scatterometers, thereby minimizing scattering and ghost images produced in the sensing branch. Furthermore, such a catadioptric optical system has smaller dimensions and weight compared to conventional scatterometers.

Before providing additional details of catadioptric optical systems according to one or more embodiments of the present invention, it is first helpful to describe an example lithography environment and scatterometry system in which such catadioptric optical systems may be used.

II. Example Lithography Environment

FIG. 1 schematically depicts the lithographic apparatus 1 of one embodiment of the invention. The apparatus comprises an illumination system IL, a patterning device PD, a substrate table WT, and a projection system PS. The illumination system (illuminator) IL is configured to condition a radiation beam B (e.g., UV radiation).

It is to be appreciated that, although the description is directed to lithography, the patterned device PD can be formed in a display system (e.g., in a LCD television or projector), without departing from the scope of the present invention. Thus, the projected patterned beam can be projected onto many different types of objects, e.g., substrates, display devices, etc.

The substrate table WT is constructed to support a substrate (e.g., a resist-coated substrate) W and connected to a positioner PW configured to accurately position the substrate in accordance with certain parameters.

The projection system (e.g., a refractive projection lens system) PS is configured to project the beam of radiation modulated by the array of individually controllable elements onto a target portion C (e.g., comprising one or more dies) of the substrate W. The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein can be considered as synonymous with the more general term "projection system."

The illumination system can include various types of optical components, such as refractive, reflective, magnetic, electromagnetic, electrostatic or other types of optical components, or any combination thereof, for directing, shaping, or controlling radiation.

The patterning device PD (e.g., a reticle or mask or an array of individually controllable elements) modulates the beam. In general, the position of the array of individually controllable elements will be fixed relative to the projection system PS. However, it can instead be connected to a positioner configured to accurately position the array of individually controllable elements in accordance with certain parameters.

The term "patterning device" or "contrast device" used herein should be broadly interpreted as referring to any device that can be used to modulate the cross-section of a radiation beam, such as to create a pattern in a target portion of the substrate. The devices can be either static patterning devices (e.g., masks or reticles) or dynamic (e.g., arrays of programmable elements) patterning devices. For brevity, most of the description will be in terms of a dynamic patterning device, however it is to be appreciated that a static pattern device can also be used without departing from the scope of the present invention.

It should be noted that the pattern imparted to the radiation beam may not exactly correspond to the desired pattern in the target portion of the substrate, for example if the pattern includes phase-shifting features or so called assist features. Similarly, the pattern eventually generated on the substrate cannot correspond to the pattern formed at any one instant on the array of individually controllable elements. This can be the case in an arrangement in which the eventual pattern formed on each part of the substrate is built up over a given period of time or a given number of exposures during which the pattern on the array of individually controllable elements and/or the relative position of the substrate changes.

Generally, the pattern created on the target portion of the substrate will correspond to a particular functional layer in a device being created in the target portion, such as an integrated circuit or a flat panel display (e.g., a color filter layer in a flat panel display or a thin film transistor layer in a flat panel display). Examples of such patterning devices include reticles, programmable mirror arrays, laser diode arrays, light emitting diode arrays, grating light valves, and LCD arrays.

Patterning devices whose pattern is programmable with the aid of electronic means (e.g., a computer), such as patterning devices comprising a plurality of programmable elements (e.g., all the devices mentioned in the previous sentence except for the reticle), are collectively referred to herein as "contrast devices." The patterning device comprises at least 10, at least 100, at least 1,000, at least 10,000, at least 100,000, at least 1,000,000, or at least 10,000,000 programmable elements.

A programmable mirror array can comprise a matrix-addressable surface having a viscoelastic control layer and a reflective surface. The basic principle behind such an apparatus is that addressed areas of the reflective surface reflect incident light as diffracted light, whereas unaddressed areas reflect incident light as undiffracted light. Using an appropriate spatial filter, the undiffracted light can be filtered out of the reflected beam, leaving only the diffracted light to reach the substrate. In this manner, the beam becomes patterned according to the addressing pattern of the matrix-addressable surface.

It will be appreciated that, as an alternative, the filter can filter out the diffracted light, leaving the undiffracted light to reach the substrate.

An array of diffractive optical MEMS devices (micro-electro-mechanical system devices) can also be used in a corresponding manner. In one example, a diffractive optical MEMS device composes a plurality of reflective ribbons that can be deformed relative to one another to form a grating that reflects incident light as diffracted light.

A further alternative example of a programmable mirror array employs a matrix arrangement of tiny mirrors, each of which can be individually tilted about an axis by applying a suitable localized electric field, or by employing piezoelectric actuation means. Once again, the mirrors are matrix-addressable, such that addressed mirrors reflect an incoming radiation beam in a different direction than unaddressed mirrors; in this manner, the reflected beam can be patterned according to the addressing pattern of the matrix-addressable mirrors. The required matrix addressing can be performed using suitable electronic means.

Another example patterning device is a programmable LCD array.

The lithographic apparatus can comprise one or more contrast devices. For example, it can have a plurality of arrays of individually controllable elements, each controlled independently of each other. In such an arrangement, some or all of the arrays of individually controllable elements can have at least one of a common illumination system (or part of an illumination system), a common support structure for the arrays of individually controllable elements, and/or a common projection system (or part of the projection system).

In one example, such as the embodiment depicted in FIG. 1, the substrate W has a substantially circular shape, optionally with a notch and/or a flattened edge along part of its perimeter. In another example, the substrate has a polygonal shape, e.g., a rectangular shape.

Examples where the substrate has a substantially circular shape include examples where the substrate has a diameter of at least 25 mm, at least 50 mm, at least 75 mm, at least 100 mm, at least 125 mm, at least 150 mm, at least 175 mm, at least 200 mm, at least 250 mm, or at least 300 mm. Alternatively, the substrate has a diameter of at most 500 mm, at most 400 mm, at most 350 mm, at most 300 mm, at most 250 mm, at most 200 mm, at most 150 mm, at most 100 mm, or at most 75 mm.

Examples where the substrate is polygonal, e.g., rectangular, include examples where at least one side, at least 2 sides or at least 3 sides, of the substrate has a length of at least 5 cm, at least 25 cm, at least 50 cm, at least 100 cm, at least 150 cm, at least 200 cm, or at least 250 cm.

At least one side of the substrate has a length of at most 1000 cm, at most 750 cm, at most 500 cm, at most 350 cm, at most 250 cm, at most 150 cm, or at most 75 cm.

In one example, the substrate W is a wafer, for instance a semiconductor wafer. The wafer material can be selected from the group consisting of Si, SiGe, SiGeC, SiC, Ge, GaAs, InP, and InAs. The wafer can be: a III/V compound semiconductor wafer, a silicon wafer, a ceramic substrate, a glass substrate, or a plastic substrate. The substrate can be transparent (for the naked human eye), colored, or absent a color.

The thickness of the substrate can vary and, to an extent, can depend on the substrate material and/or the substrate dimensions. The thickness can be at least 50 µm, at least 100 µm, at least 200 µm, at least 300 µm, at least 400 µm, at least 500 µm, or at least 600 µm. Alternatively, the thickness of the substrate can be at most 5000 µm, at most 3500 µm, at most 2500 µm, at most 1750 µm, at most 1250 µm, at most 1000 µm, at most 800 µm, at most 600 µm, at most 500 µm, at most 400 µm, or at most 300 µm.

The substrate referred to herein can be processed, before or after exposure, in for example a track (a tool that typically applies a layer of resist to a substrate and develops the exposed resist), a metrology tool, and/or an inspection tool. In one example, a resist layer is provided on the substrate.

The projection system can image the pattern on the array of individually controllable elements, such that the pattern is coherently formed on the substrate. Alternatively, the projection system can image secondary sources for which the elements of the array of individually controllable elements act as shutters. In this respect, the projection system can comprise an array of focusing elements such as a micro lens array (known as an MLA) or a Fresnel lens array to form the secondary sources and to image spots onto the substrate. The array of focusing elements (e.g., MLA) comprises at least 10 focus elements, at least 100 focus elements, at least 1,000 focus elements, at least 10,000 focus elements, at least 100,000 focus elements, or at least 1,000,000 focus elements.

The number of individually controllable elements in the patterning device is equal to or greater than the number of focusing elements in the array of focusing elements. One or more (e.g., 1,000 or more, the majority, or each) of the focusing elements in the array of focusing elements can be optically associated with one or more of the individually controllable elements in the array of individually controllable elements, with 2 or more, 3 or more, 5 or more, 10 or more, 20 or more, 25 or more, 35 or more, or 50 or more of the individually controllable elements in the array of individually controllable elements.

The MLA can be movable (e.g., with the use of one or more actuators) at least in the direction to and away from the substrate. Being able to move the MLA to and away from the substrate allows, e.g., for focus adjustment without having to move the substrate.

Figure 2:
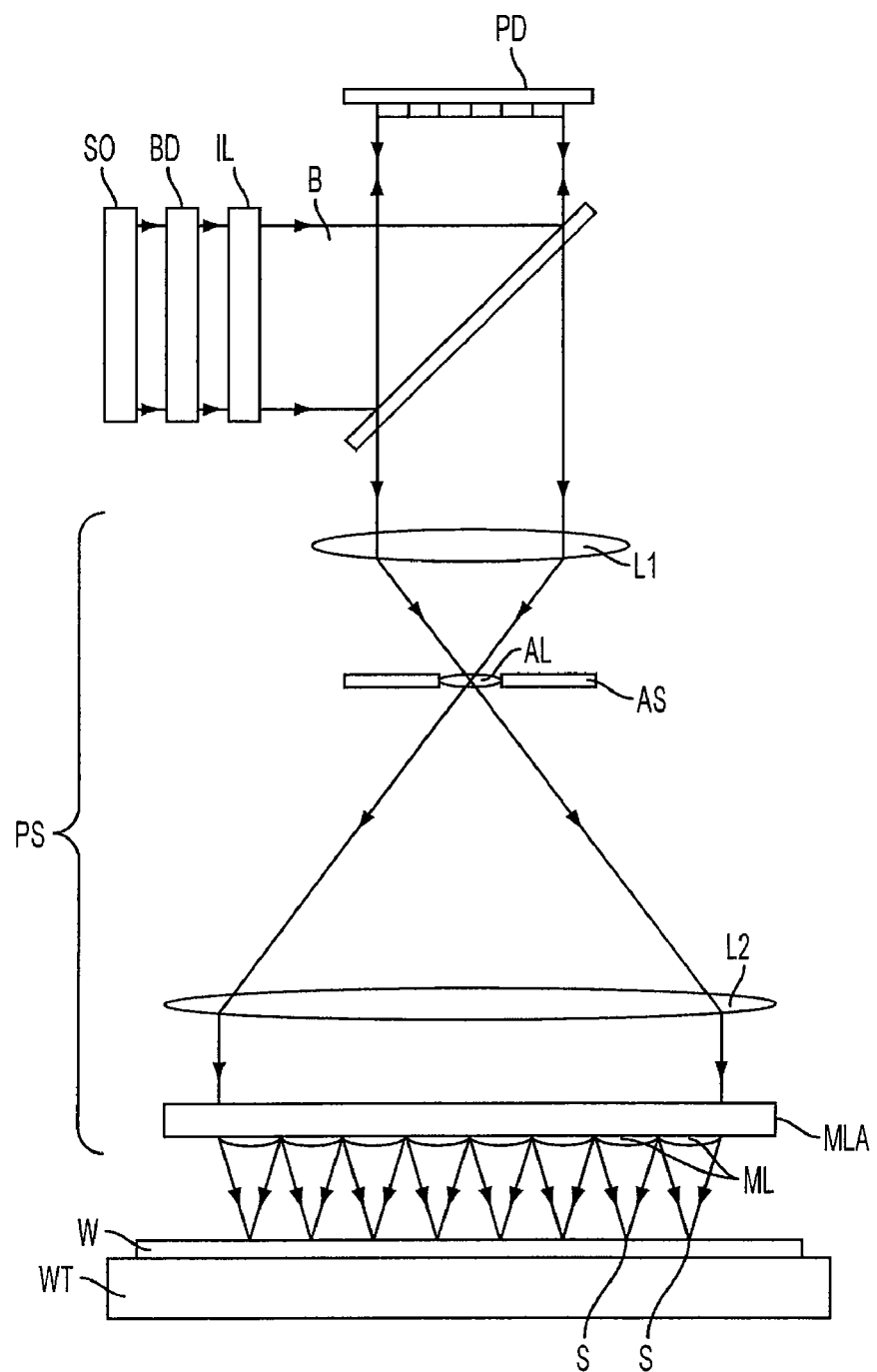

As herein depicted in FIGS. 1 and 2, the apparatus is of a reflective type (e.g., employing a reflective array of individually controllable elements). Alternatively, the apparatus can be of a transmission type (e.g., employing a transmission array of individually controllable elements).

The lithographic apparatus can be of a type having two (dual stage) or more substrate tables. In such "multiple stage" machines, the additional tables can be used in parallel, or preparatory steps can be carried out on one or more tables while one or more other tables are being used for exposure.

The lithographic apparatus can also be of a type wherein at least a portion of the substrate can be covered by an "immersion liquid" having a relatively high refractive index, e.g., water, so as to fill a space between the projection system and the substrate. An immersion liquid can also be applied to other spaces in the lithographic apparatus, for example, between the patterning device and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring again to FIG. 1, the illuminator IL receives a radiation beam from a radiation source SO. The radiation source provides radiation having a wavelength of at least 5 nm, at least 10 nm, at least 11-13 nm, at least 50 nm, at least 100 nm, at least 150 nm, at least 175 nm, at least 200 nm, at least 250 nm, at least 275 nm, at least 300 nm, at least 325 nm, at least 350 nm, or at least 360 nm. Alternatively, the radiation provided by radiation source SO has a wavelength of at most 450 nm, at most 425 nm, at most 375 nm, at most 360 nm, at most 325 nm, at most 275 nm, at most 250 nm, at most 225 nm, at most 200 nm, or at most 175 nm. The radiation can have a wavelength including 436 nm, 405 nm, 365 nm, 355 nm, 248 nm, 193 nm, 157 nm, and/or 126 nm.

The source and the lithographic apparatus can be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source can be an integral part of the lithographic apparatus, for example when the source is a mercury lamp. The source SO and the illuminator IL, together with the beam delivery system BD if required, can be referred to as a radiation system.

The illuminator IL, can comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL can comprise various other components, such as an integrator IN and a condenser CO. The illuminator can be used to condition the radiation beam to have a desired uniformity and intensity distribution in its cross-section. The illuminator IL, or an additional component associated with it, can also be arranged to divide the radiation beam into a plurality of sub-beams that can, for example, each be associated with one or a plurality of the individually controllable elements of the array of individually controllable elements. A two-dimensional diffraction grating can, for example, be used to divide the radiation beam into sub-beams. In the present description, the terms "beam of radiation" and "radiation beam" encompass, but are not limited to, the situation in which the beam is comprised of a plurality of such sub-beams of radiation.

The radiation beam B is incident on the patterning device PD (e.g., an array of individually controllable elements) and is modulated by the patterning device. Having been reflected by the patterning device PD, the radiation beam B passes through the projection system PS, which focuses the beam onto a target portion C of the substrate W. With the aid of the positioner PW and position sensor IF2 (e.g., an interferometric device, linear encoder, capacitive sensor, or the like), the substrate table WT can be moved accurately, e.g., so as to position different target portions C in the path of the radiation beam B. Where used, the positioning means for the array of individually controllable elements can be used to correct accurately the position of the patterning device PD with respect to the path of the beam B. e.g., during a scan.

In one example, movement of the substrate table WT is realized with the aid of a long-stroke module (course positioning) and a short-stroke module (fine positioning), which are not explicitly depicted in FIG. 1. In another example, a short stroke stage cannot be present. A similar system can also be used to position the array of individually controllable elements. It will be appreciated that the beam B can alternatively/additionally be moveable, while the object table and/or the array of individually controllable elements can have a fixed position to provide the required relative movement. Such an arrangement can assist in limiting the size of the apparatus. As a further alternative, which can, e.g., be applicable in the manufacture of flat panel displays, the position of the substrate table WT and the projection system PS can be fixed and the substrate W can be arranged to be moved relative to the substrate table WT. For example, the substrate table WT can be provided with a system for scanning the substrate W across it at a substantially constant velocity.

As shown in FIG. 1, the beam of radiation B can be directed to the patterning device PD by means of a beam splitter BS configured such that the radiation is initially reflected by the beam splitter and directed to the patterning device PD. It should be realized that the beam of radiation B can also be directed at the patterning device without the use of a beam splitter. The beam of radiation can be directed at the patterning device at an angle between 0 and 90°, between 5 and 85°, between 15 and 75°, between 25 and 65°, or between 35 and 55° (the embodiment shown in FIG. 1 is at a 90° angle). The patterning device PD modulates the beam of radiation B and reflects it back to the beam splitter BS which transmits the modulated beam to the projection system PS. It will be appreciated, however, that alternative arrangements can be used to direct the beam of radiation B to the patterning device PD and subsequently to the projection system PS. In particular, an arrangement such as is shown in FIG. 1 cannot be required if a transmission patterning device is used.

The depicted apparatus can be used in several modes:

1. In step mode, the array of individually controllable elements and the substrate are kept essentially stationary, while an entire pattern imparted to the radiation beam is projected onto a target portion C at one go (i.e., a single static exposure).

The substrate table WT is then shifted in the X and/or Y direction so that a different target portion C can be exposed. In step mode, the maximum size of the exposure field limits the size of the target portion C imaged in a single static exposure.

2. In scan mode, the array of individually controllable elements and the substrate are scanned synchronously while a pattern imparted to the radiation beam is projected onto a target portion C (i.e., a single dynamic exposure). The velocity and direction of the substrate relative to the array of individually controllable elements can be determined by the (de-) magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In pulse mode, the array of individually controllable elements is kept essentially stationary and the entire pattern is projected onto a target portion C of the substrate W using a pulsed radiation source. The substrate table WT is moved with an essentially constant speed such that the beam B is caused to scan a line across the substrate W. The pattern on the array of individually controllable elements is updated as required between pulses of the radiation system and the pulses are timed such that successive target portions C are exposed at the required locations on the substrate W. Consequently, the beam B can scan across the substrate W to expose the complete pattern for a strip of the substrate. The process is repeated until the complete substrate W has been exposed line by line.

4. Continuous scan mode is essentially the same as pulse mode except that the substrate W is scanned relative to the modulated beam of radiation B at a substantially constant speed and the pattern on the array of individually controllable elements is updated as the beam B scans across the substrate W and exposes it. A substantially constant radiation source or a pulsed radiation source, synchronized to the updating of the pattern on the array of individually controllable elements, can be used.

5. In pixel grid imaging mode, which can be performed using the lithographic apparatus of FIG. 2, the pattern formed on substrate W is realized by subsequent exposure of spots formed by a spot generator that are directed onto patterning device PD. The exposed spots have substantially the same shape. On substrate W the spots are printed in substantially a grid. In one example, the spot size is larger than a pitch of a printed pixel grid, but much smaller than the exposure spot grid. By varying intensity of the spots printed, a pattern is realized. In between the exposure flashes the intensity distribution over the spots is varied.

Combinations and/or variations on the above described modes of use or entirely different modes of use can also be employed.

Figure 13:
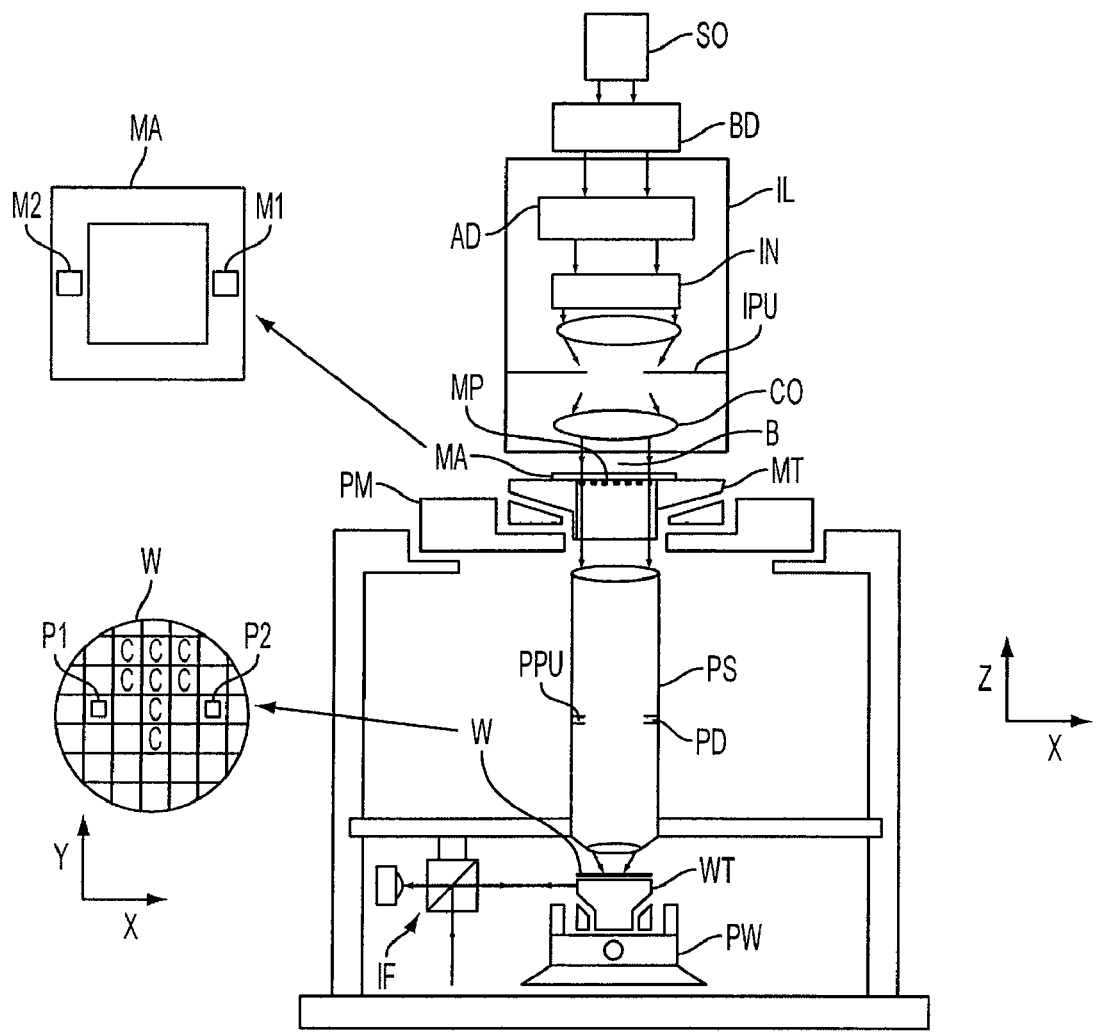
FIG. 13 depicts another lithographic apparatus.

FIG. 13 depicts a lithographic apparatus according to another embodiment of the present invention. Similar to FIGS. 1 and 2 above, the apparatus of FIG. 13 comprises an illumination system IL, a support structure MT, a substrate table WT, and a projection system.

The illumination system IL is configured to condition a radiation beam B (e.g., a beam of UV radiation as provided by a mercury arc lamp, or a beam of DUV radiation generated by a KrF excimer laser or an ArF excimer laser).

The support structure (e.g., a mask table) MT is constructed to support a patterning device (e.g., a mask) MA having a mask pattern MP and connected to a first positioner PM configured to accurately position the patterning device in accordance with certain parameters.

The substrate table (e.g., a wafer table) WT is constructed to hold a substrate (e.g., a resist coated wafer) W and connected to a second positioner PW configured to accurately position the substrate in accordance with certain parameters.

The projection system (e.g., a refractive projection lens system) PS configured to project a pattern imparted to the radiation beam B by the pattern MP of the patterning device MA onto a target portion C (e.g., comprising one or more dies) of the substrate W.

The illumination system IL may include various types of optical components, such as refractive, reflective, and diffractive types of optical components, or any combination thereof, for directing, shaping, or controlling radiation.

The support structure MT supports, i.e., bears the weight of, the patterning device MA. It holds the patterning device MA in a manner that depends on the orientation of the patterning device MA, the design of the lithographic apparatus, and other conditions, such as for example whether or not the patterning device MA is held in a vacuum environment. The support structure MT may be a frame or a table, for example, which may be fixed or movable as required. The support structure MT may ensure that the patterning device MA is at a desired position, for example with respect to the projection system PA. Any use of the terms "reticle" or "mask" herein may be considered synonymous with the more general term "patterning device."

As noted above, the term "patterning device" used herein should be broadly interpreted as referring to any device that can be used to impart a radiation beam B with a pattern in its cross-section such as to create a pattern in a target portion C of the substrate W. It should be noted that the pattern imparted to the radiation beam B may not exactly correspond to the desired pattern in the target portion C of the substrate W, for example if the pattern MP includes phase-shifting features or so called assist features. Generally, the pattern imparted to the radiation beam B will correspond to a particular functional layer in a device being created in the target portion C, such as an integrated circuit.

Referring to FIG. 13, the illumination system IL receives a radiation beam from a radiation source SO, such as for example a mercury-arc lamp for providing g-line or i-line UV radiation, or an excimer laser for providing DUV radiation of a wavelength of less than about 270 nm, such as for example 248, 193, 1137, and 126 nm. The source SO and the lithographic apparatus may be separate entities, for example when the source SO is an excimer laser. In such cases, the radiation beam B is passed from the source SO to the illumination system IL with the aid of a beam delivery system BD comprising, for example, suitable directing mirrors and/or a beam expander. In other cases the source SO may be an integral part of the lithographic apparatus, for example when the source SO is a mercury lamp. The source SO and the illumination system IL, together with the beam delivery system BD if required, may be referred to as a radiation system.

The illumination system IL may comprise an adjuster AD for adjusting the angular intensity distribution of the radiation beam B at mask level. Generally, at least the outer and/or inner radial extent (commonly referred to as σ-outer and σ-inner, respectively) of the intensity distribution in a pupil IPU of the illumination system IL can be adjusted. In addition, the illumination system IL may comprise various other components, such as an integrator IN and a condenser CO. The illumination system IL may be used to condition the radiation beam B, to have a desired uniformity and intensity distribution in its cross section at mask level.

The radiation beam B is incident on the patterning device (e.g., mask MA), which is held on the support structure (e.g., mask table MT), and is patterned by the patterning device MA in accordance with a pattern MP. Having traversed the mask MA, the radiation beam B passes through the projection system PS, which focuses the beam B onto a target portion C of the substrate W.

The projection system has a pupil PPU conjugate to the illumination system pupil IPU. Portions of radiation emanate from the intensity distribution at the illumination system pupil IPU and traverse a mask pattern without being affected by diffraction at a mask pattern create an image of the intensity distribution at the illumination system pupil IPU.

With the aid of the second positioner PW and position sensor IF (e.g., an interferometric device, linear encoder or capacitive sensor), the substrate table WT can be moved accurately, e.g., so as to position different target portions C in the path of the radiation beam B. Similarly, the first positioner PM and another position sensor (which is not explicitly depicted in FIG. 13) can be used to accurately position the mask MA with respect to the path of the radiation beam B. e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks P1, P2 as illustrated occupy dedicated target portions, they may be located in spaces between target portions (these are known as scribe-lane alignment marks). Similarly, in situations in which more than one die is provided on the mask MA, the mask alignment marks M1 and M2 may be located between the dies.

The depicted apparatus of FIG. 13 could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

In lithography, a pattern is exposed on a layer of resist on the substrate. The resist is then developed. Subsequently, additional processing steps are performed on the substrate. The effect of these subsequent processing steps on each portion of the substrate depends on the exposure of the resist. In particular, the processes are tuned such that portions of the substrate that receive a radiation dose above a given dose threshold respond differently to portions of the substrate that receive a radiation dose below the dose threshold. For example, in an etching process, areas of the substrate that receive a radiation dose above the threshold are protected from etching by a layer of developed resist. However, in the post-exposure development, the portions of the resist that receive a radiation dose below the threshold are removed and therefore those areas are not protected from etching. Accordingly, a desired pattern can be etched. In particular, the individually controllable elements in the patterning device are set such that the radiation that is transmitted to an area on the substrate within a pattern feature is at a sufficiently high intensity that the area receives a dose of radiation above the dose threshold during the exposure. The remaining areas on the substrate receive a radiation dose below the dose threshold by setting the corresponding individually controllable elements to provide a zero or significantly lower radiation intensity.

In practice, the radiation dose at the edges of a pattern feature does not abruptly change from a given maximum dose to zero dose even if the individually controllable elements are set to provide the maximum radiation intensity on one side of the feature boundary and the minimum radiation intensity on the other side. Instead, due to diffractive effects, the level of the radiation dose drops off across a transition zone. The position of the boundary of the pattern feature ultimately formed by the developed resist is determined by the position at which the received dose drops below the radiation dose threshold. The profile of the drop-off of radiation dose across the transition zone, and hence the precise position of the pattern feature boundary, can be controlled more precisely by setting the individually controllable elements that provide radiation to points on the substrate that are on or near the pattern feature boundary. These can be not only to maximum or minimum intensity levels, but also to intensity levels between the maximum and minimum intensity levels. This is commonly referred to as "grayscaling."

Grayscaling provides greater control of the position of the pattern feature boundaries than is possible in a lithography system in which the radiation intensity provided to the substrate by a given individually controllable element can only be set to two values (e.g., just a maximum value and a minimum value). At least 3, at least 4 radiation intensity values, at least 8 radiation intensity values, at least 16 radiation intensity values, at least 32 radiation intensity values, at least 64 radiation intensity values, at least 128 radiation intensity values, or at least 256 different radiation intensity values can be projected onto the substrate.

It should be appreciated that grayscaling can be used for additional or alternative purposes to that described above. For example, the processing of the substrate after the exposure can be tuned, such that there are more than two potential responses of regions of the substrate, dependent on received radiation dose level. For example, a portion of the substrate receiving a radiation dose below a first threshold responds in a first manner; a portion of the substrate receiving a radiation dose above the first threshold but below a second threshold responds in a second manner; and a portion of the substrate receiving a radiation dose above the second threshold responds in a third manner. Accordingly, grayscaling can be used to provide a radiation dose profile across the substrate having more than two desired dose levels. The radiation dose profile can have at least 2 desired dose levels, at least 3 desired radiation dose levels, at least 4 desired radiation dose levels, at least 6 desired radiation dose levels or at least 8 desired radiation dose levels.

It should further be appreciated that the radiation dose profile can be controlled by methods other than by merely controlling the intensity of the radiation received at each point on the substrate, as described above. For example, the radiation dose received by each point on the substrate can alternatively or additionally be controlled by controlling the duration of the exposure of the point. As a further example, each point on the substrate can potentially receive radiation in a plurality of successive exposures. The radiation dose received by each point can, therefore, be alternatively or additionally controlled by exposing the point using a selected subset of the plurality of successive exposures.

FIG. 2 depicts an arrangement of the apparatus according to the present invention that can be used, e.g., in the manufacture of flat panel displays. Components corresponding to those shown in FIG. 1 are depicted with the same reference numerals. Also, the above descriptions of the various embodiments, e.g., the various configurations of the substrate, the contrast device, the MLA, the beam of radiation, etc., remain applicable.

As shown in FIG. 2, the projection system PS includes a beam expander, which comprises two lenses L1, L2. The first lens L1 is arranged to receive the modulated radiation beam B and focus it through an aperture in an aperture stop AS. A further lens AL can be located in the aperture. The radiation beam B then diverges and is focused by the second lens L2 (e.g., a field lens).

The projection system PS further comprises an array of lenses MLA arranged to receive the expanded modulated radiation B. Different portions of the modulated radiation beam B, corresponding to one or more of the individually controllable elements in the patterning device PD, pass through respective different lenses ML in the array of lenses MLA. Each lens focuses the respective portion of the modulated radiation beam B to a point which lies on the substrate W. In this way an array of radiation spots S is exposed onto the substrate W. It will be appreciated that, although only eight lenses of the illustrated array of lenses 14 are shown, the array of lenses can comprise many thousands of lenses (the same is true of the array of individually controllable elements used as the patterning device PD).

III. Example Catadioptric Optical Systems Used for Scatterometry in Accordance with Embodiments of the Present Invention A catadioptric optical system in accordance with an embodiment of the present invention may be used in a scatterometry system to sense or detect properties of the surface of substrate.

Figure 3A:
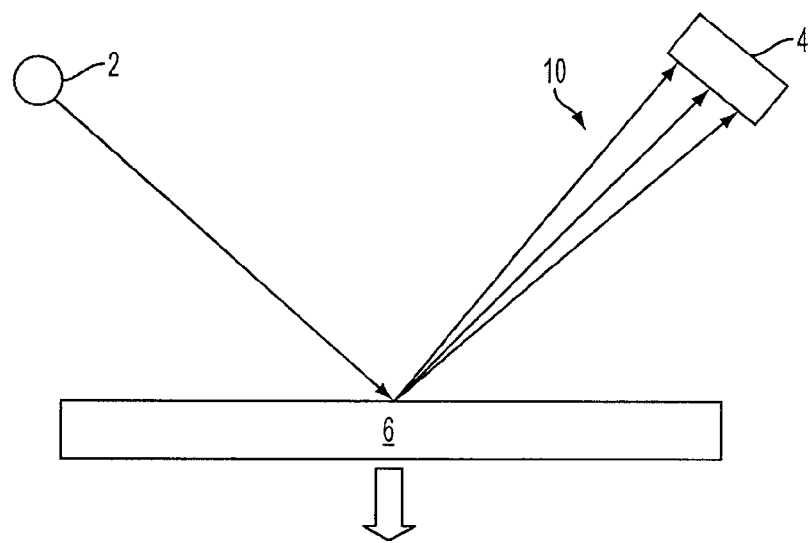
Figure 3B:
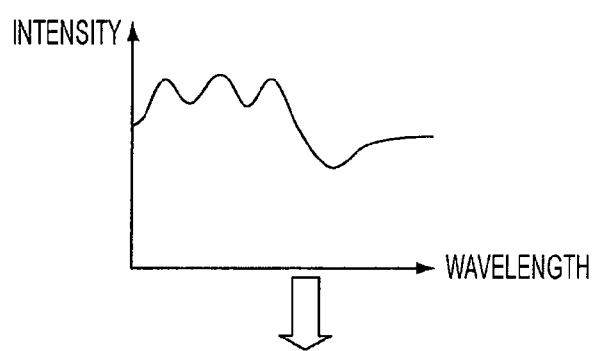
Figure 3C:
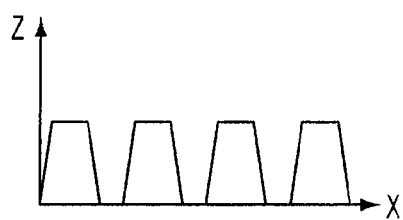

FIG. 3A depicts a scatterometer by which one or more properties of the surface of a substrate 6 may be determined. In an embodiment, the scatterometer comprises a radiation source 2 (e.g., a broadband (white light) radiation source), which directs radiation onto a substrate 6. The reflected radiation is passed to a sensor 4 (e.g., a spectrometer detector) which measures a spectrum 10 (intensity as a function of wavelength) of the specular reflected radiation. From this data, the structure or profile giving rise to the detected spectrum may be reconstructed, e.g., by Rigorous Coupled Wave Analysis and non-linear regression or by comparison with a library of simulated spectra, as shown in FIGS. 3B and 3C. In general, for the reconstruction, the general form of the structure is known and some parameters are assumed from knowledge of the process by which the structure was made, leaving only a few parameters of the structure to be determined from the scatterometry data.

The scatterometer may be a normal-incidence scatterometer or an oblique-incidence scatterometer. Variants of scatterometry may also be used in which the reflection is measured at a range of angles of a single wavelength, rather than the reflection at a single angle of a range of wavelengths.

Figure 4:
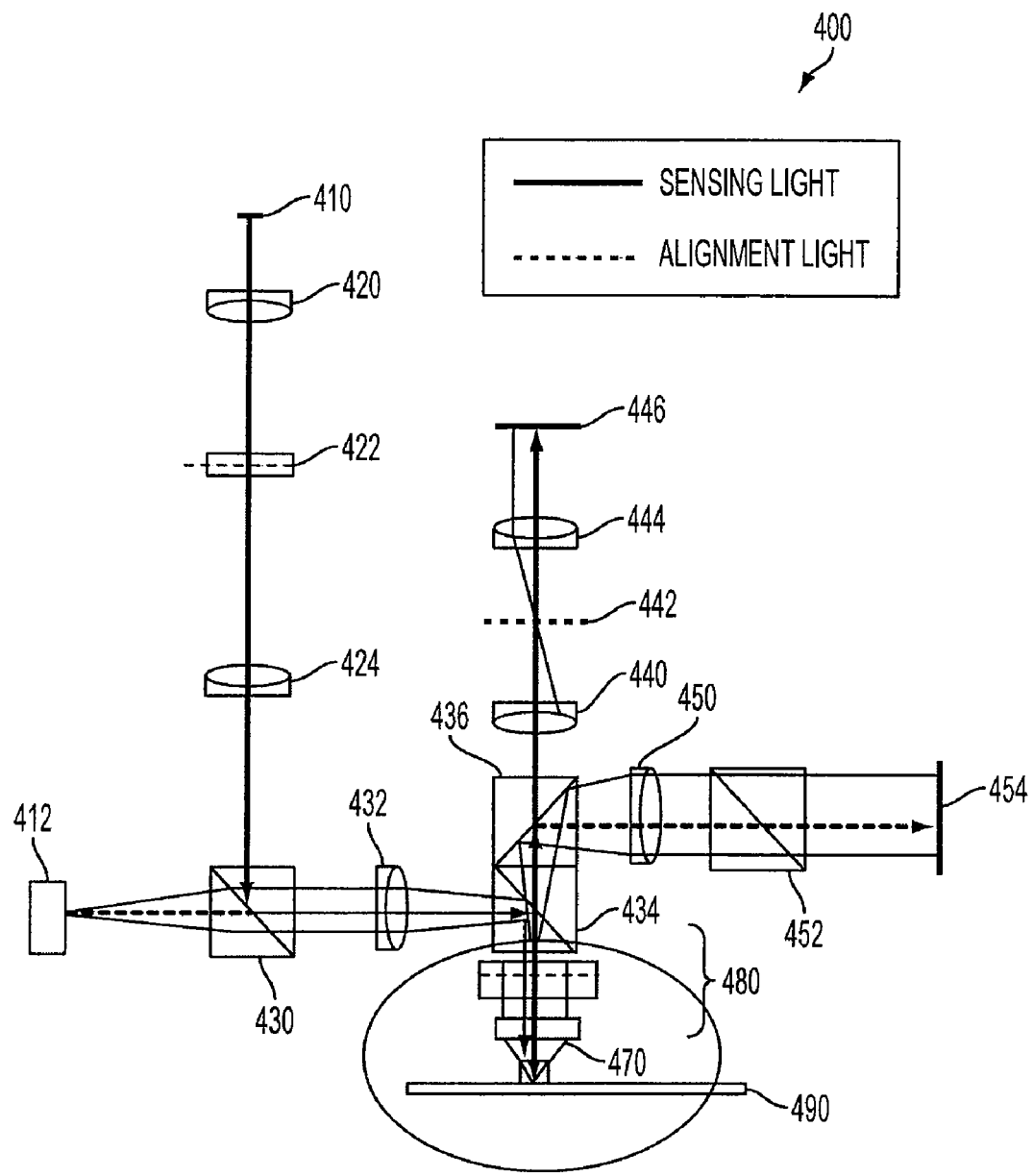
FIG. 4 depicts a sensing and alignment system including a catadioptric optical objective in accordance with an embodiment of the present invention.

FIG. 4 depicts a scatterometry system 400 that can sense one or more properties of the surface of wafer 490. System 400 has an alignment branch and a sensing branch that both share a catadioptric optical system 480. To operate properly, the alignment and sensing branches have very different optical specifications, because they use different illumination sources and perform different functions. Importantly, catadioptric optical system 480 functions properly within the optical specifications of both the alignment branch and the sensing branch. In the embodiment depicted in FIG. 4, catadioptric optical system 480 includes a optical element 434 and an objective system 470. The alignment branch, sensing branch, and catadioptric optical system 480 are described in more detail below.

The alignment branch is used to align system 400 with features on a wafer 490. The alignment branch includes an illumination source 412 (such as a wide band light emitting diode (LED)) that provides a first beam of electromagnetic radiation. In an example, the first beam has a spectral range between 450 nanometers and 600 nanometers. The first beam passes through optical elements 430 and 432 and then impinges on an optical element 434. The first beam is then directed through objective 470 and focused on a portion of wafer 490. The first beam is then reflected back through objective 470 and optical element 434. A beam splitter 436 directs the first beam through a focusing lens 450 and beam splitter 452, and then onto a first sensor 454 (e.g., a charge coupled device (CCD)). The image of wafer 490, provided by sensor 454, is used to align system 400 with specific portions of wafer 490.

The sensing branch is used to sense or detect the features on the aligned portions of wafer 490 according to known scatterometry techniques, such as the scatterometry techniques described above. The sensing branch includes an illumination source 410 (such as a tungsten illumination source having an interference filter) that provides a second beam of electromagnetic radiation. In an example, the second beam has a bandwidth of approximately 10 nanometers and falls within the spectral range of approximately 300 nanometers to 800 nanometers. The second beam passes through optical elements 420, 422, 424, 430 and lens 432. Optical element 434 then directs the second beam through objective system 470 and onto an aligned portion of wafer 490. The second beam is reflected and/or refracted by the aligned portion of wafer 490 and directed back through objective system 470 and optical element 434. The second beam also passes through beam splitter 436, lens 440, aperture 442, and lens 444, and then impinges on a second detector 446 (e.g., second CCD). Second detector 446 provides an image of the aligned portion of wafer 490 that is used to detect features on the surface of wafer 490.

As mentioned above, catadioptric optical system 480 includes optical element 434 and objective system 470. Catadioptric optical system 480 is achromatic in a wide spectral range (such as about 200 nanometers to 1000 nanometers). When used in system 400, catadioptric optical system 480 has low obscuration in the sensing branch (such as approximately 14% by radius) and substantially no obscuration in the alignment branch. It has smaller dimensions and weight, and only a few surfaces thereby reducing scatter and eliminating ghost images.

Figure 5:
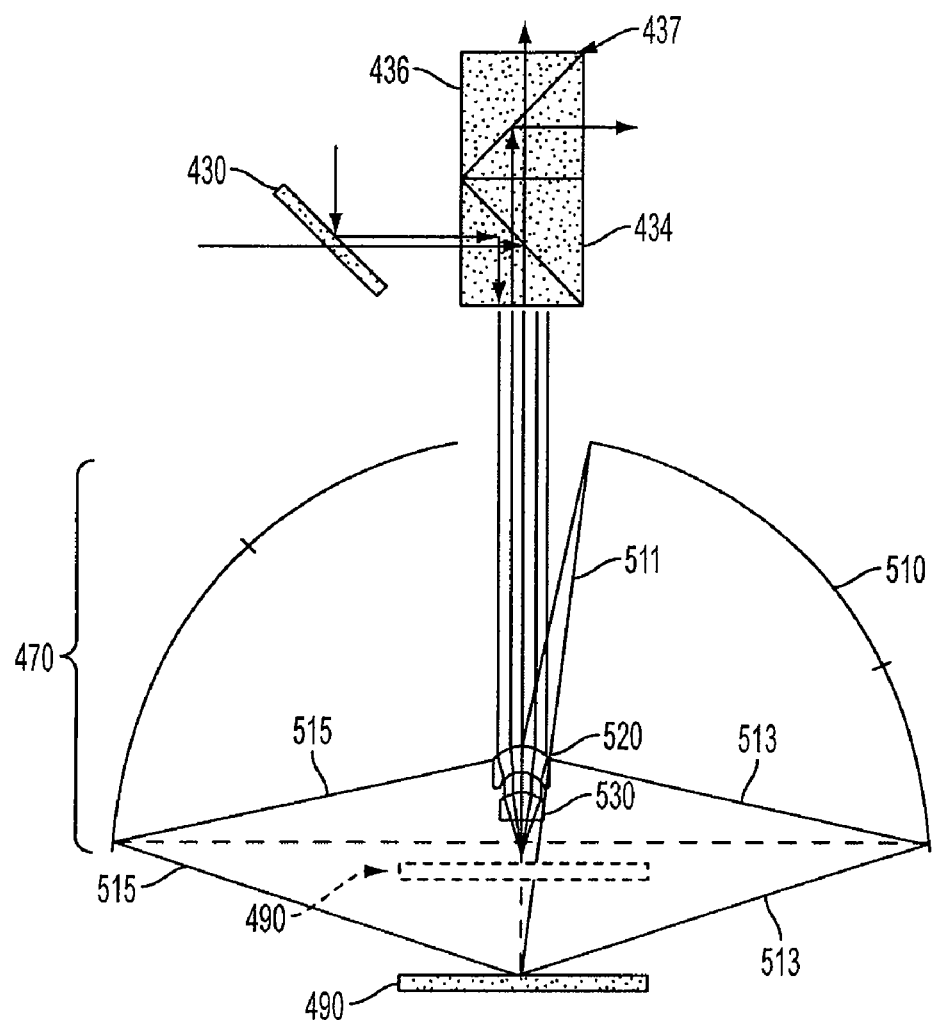
FIG. 5 depicts details of the catadioptric optical objective of FIG. 4.

FIG. 5 depicts details of objective system 470 according to one embodiment. As illustrated in FIG. 5, objective system 470 includes a convex spherical surface 520, a concave aspherical surface 510, and a lens 530. Spherical surface 520 is conditioned (e.g., coated) to cause it to have (i) refractive properties for the electromagnetic radiation from the alignment branch and (ii) reflective properties for the electromagnetic radiation from the sensing branch. That is, the refractive properties of convex spherical surface 520 and lens 530 are used for alignment, while the reflective properties of convex spherical surface 520 and concave aspherical surface 510 are used for sensing, as described in more detail below.

For alignment purposes, wafer 490 is positioned closer to lens 530, as depicted by the ghost image of wafer 490. The first beam of electromagnetic radiation (used for alignment) passes through a hole in concave aspherical surface 510, through convex spherical surface 520, and is focused by lens 530 onto wafer 490. The first beam is then reflected off wafer 490 and passes through the alignment branch to first CCD 454 (not shown, see FIG. 4) as described above.

For sensing purposes, wafer 490 is positioned farther from lens 530, as depicted by the solid image of wafer 490. The second beam of electromagnetic radiation (used for sensing) passes through the hole in concave aspherical surface 510, reflects off of convex spherical surface 520, and impinges on a reflective portion of concave aspherical surface 510. The reflective portion of concave aspherical surface 510 focuses the second beam onto wafer 490. For example, three example rays 511, 513, and 515 are shown reflecting off of convex surface 520 and concave aspherical surface 510 and being focused onto wafer 490. Importantly, when used for sensing, objective system 470 can have a high numerical aperture (such as, for example, approximately 0.90 or 0.95) and does not include any refractive elements. As a result, objective system 470 operates properly over a wide spectral range (such as about 200 nanometers to 1000 nanometers).

Thus, beam splitters 437, 434 and objective 470 comprise a catadioptric optical system that may be used in a scatterometer in accordance with an embodiment of the present invention. Additional catadioptric optical systems in accordance with embodiments of the present invention are described below.

An achromatic, high numerical aperture catadioptric optical system in accordance with an embodiment of the present invention includes a convex spherical surface and a concave aspherical surface positioned to receive electromagnetic radiation from the convex spherical surface. The convex aspheric surface is designed according to the following aspheric equation $$Z(r) = \frac{cr^2}{1 + \sqrt{1 - (1+K)c^2 r^2}} + Ar^4 + Br^6 + Cr^8 + Dr^{10} + Er^{12} + Fr^{14} + Gr^{16} + Hr^{18} + Jr^{20} \quad \text{(Eq. 1)}$$

wherein:

$r^2 = x^2 + y^2$;

c is the curvature at the pole of the surface;

K is the conic constant; and

A through J are the 4th through 20th order deformation terms.

There are several embodiments for designing a catadioptric optical system as illustrated for example in FIGS. 6-9 and 12. In each of the embodiments depicted in FIGS. 6-9 and 12, collimated electromagnetic radiation from an illuminator is focused onto a small spot (such as approximately 10 microns) on a substrate (e.g., a wafer). Each embodiment can be used for scatterometry, and each embodiment has an extremely wide numerical aperture (such as a numerical aperture of approximately 0.95) and operates in a wide spectral range (such as about 200 nanometers to 1000 nanometers). As shown in FIGS. 6-9 and 12, each embodiment includes a correcting plate before a concave aspherical surface. Each of these embodiments is described in more detail below.

Figure 6:
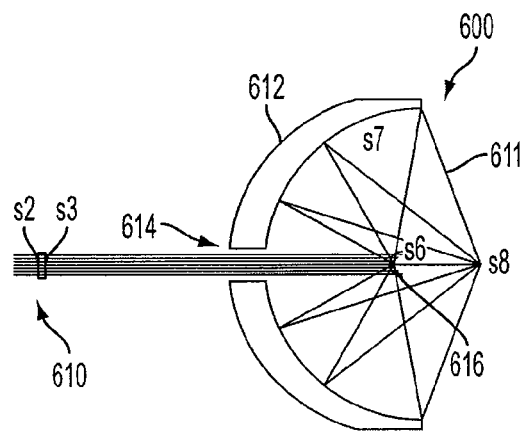
FIGS. 6-9 depict various catadioptric optical systems in accordance with embodiments of the present invention.

FIG. 6 depicts an example catadioptric optical system 600 in accordance with an embodiment of the present invention. As shown in FIG. 6, catadioptric optical system 600 includes a correcting plate 610, a spherical convex mirror 616, and an aspherical concave mirror 612.

Correcting plate 610 conditions a beam of electromagnetic radiation to correct one or more optical aberrations (such as coma). As shown in FIG. 6, correcting plate 610 includes an aspherical surface s2 and a spherical surface s3.

Spherical convex mirror 616 comprises a spherical reflective surface s6 that is positioned to reflect the electromagnetic radiation conditioned by correcting plate 610. Electromagnetic radiation conditioned by correcting plate 610 passes through a hole 614 in aspherical concave mirror 612 and impinges on spherical convex mirror 616. Spherical convex mirror 616 can be positioned on mechanical supports in air with respect to a wafer (not specifically illustrated in FIG. 6).

Aspherical concave mirror 612 receives the electromagnetic radiation reflected by spherical reflective surface s6. Aspherical concave mirror 612 comprises an aspherical reflective surface s7 that focuses this electromagnetic radiation on a target portion of the wafer. For example, an example ray 611 reflected by aspherical reflective surface s7 is depicted in FIG. 6.

An example prescription for designing the optical surfaces depicted in the embodiment of FIG. 6 is set forth below in Table 1.

TABLE 1

|     | Surface type | Radius   | Thickness | Glass  |
|-----|--------------|----------|-----------|--------|
| s1  |              | infinity | 25.000    |        |
| s2  | Asphere 1    | −88.929  | 1.800     | SIO2   |
| s3  |              | −92.223  | 103.344   |        |
| s4  |              | infinity | 0.000     |        |
| s6  |              | 4.281    | −37.510   | mirror |
| s7  | Asphere 2    | 49.277   | 52.495    | mirror |
| s8  |              | infinity | 12.587    |        |

Aspheric surfaces s2 and s6 of the embodiment depicted in FIG. 6 are defined by Eq. 1 in accordance with the parameters set forth below in Table 2.

TABLE 2

|                          | Asphere 1  | Asphere 2  |
|--------------------------|------------|------------|
| Y Radius                 | −88.9295   | 49.27722   |
| Conic Constant (K)       | −345.515   | −0.04662   |
| 4th Order Coefficient (A)| −2.87E−05  | −1.69E−09  |
| 6th Order Coefficient (B)| 1.02E−06   | 7.50E−12   |
| 8th Order Coefficient (C)| −1.13E−07  | −1.12E−14  |
| 10th Order Coefficient (D)| 8.26E−10  | 7.63E−18   |
| 12th Order Coefficient (E)| 0         | −1.35E−21  |
| 14th Order Coefficient (F)| 0         | −1.06E−24  |
| 16th Order Coefficient (G)| 0         | 5.91E−28   |
| 18th Order Coefficient (H)| 0         | −8.79E−32  |
| 20th Order Coefficient (J)| 0         | 0          |

Figure 7:
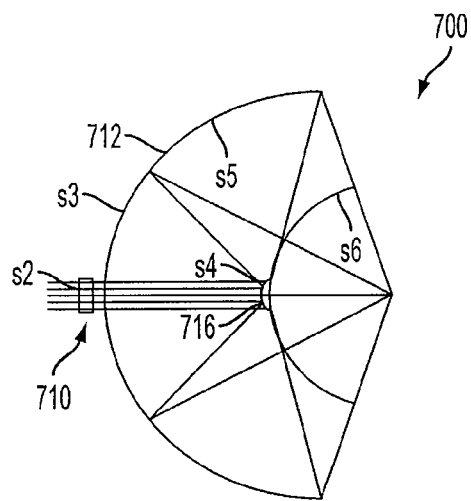

FIG. 7 depicts an example catadioptric optical system 700 in accordance with another embodiment of the present invention. As shown in FIG. 7, catadioptric optical system 700 includes a correcting plate 710, a spherical convex mirror 716, and a monolithic glass element 712.

Correcting plate 710 conditions a beam of electromagnetic radiation to correct one or more optical aberrations (such as coma). Correcting plate 710 includes an aspherical surface s2.

Figure 14:
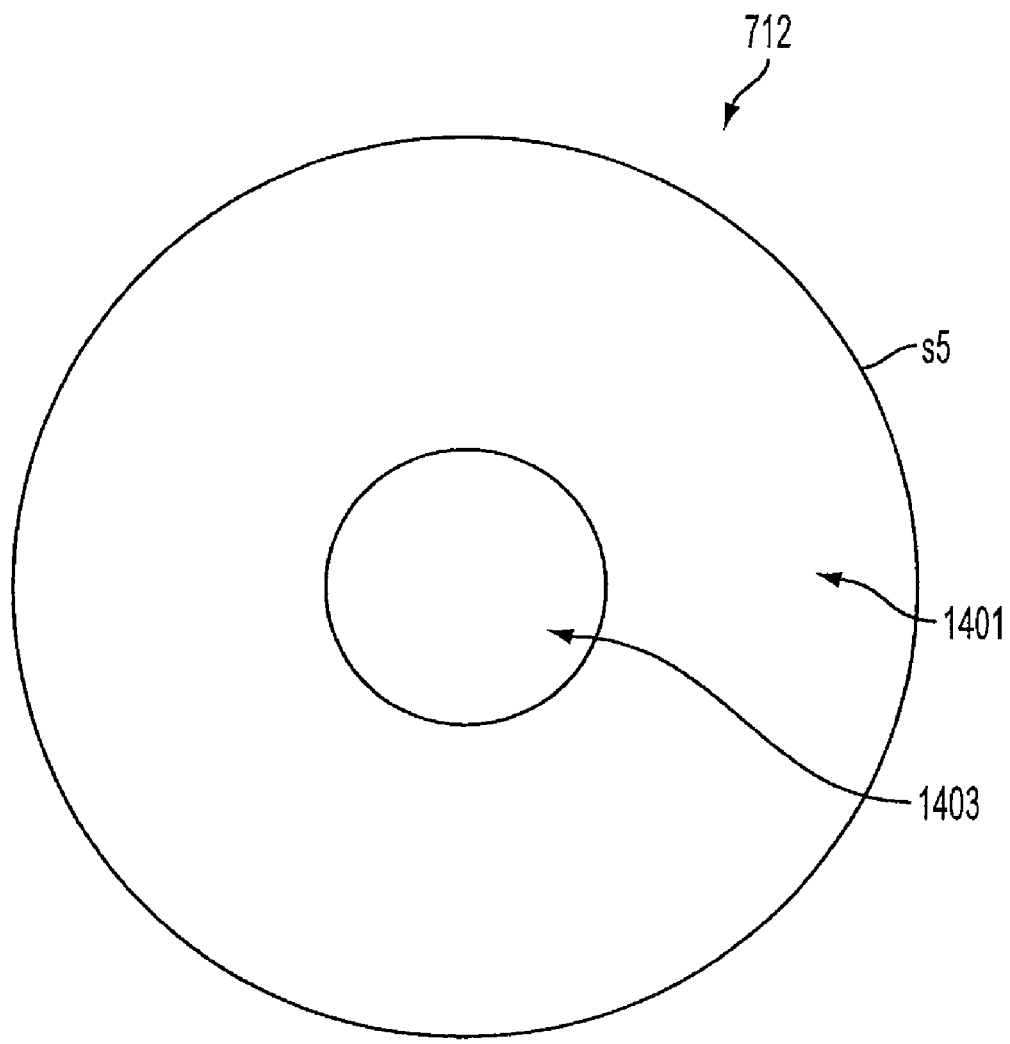
FIG. 14 depicts a plan view of a surface included in the catadioptric optical system of FIG. 7.

Spherical convex mirror 716 comprises a spherical reflective surface s4 that is positioned to reflect the electromagnetic radiation conditioned by correcting plate 710. In the embodiment depicted in FIG. 7, spherical convex mirror 716 is positioned on a surface s6 of monolithic glass element 712. As illustrated in FIG. 14, aspheric surface s5 of monolithic glass element 712 has a reflective portion 1401 and a transparent portion 1403. Transparent portion 1403 is centered around the optical axis and has a diameter that is based the width of the input beam. As a result, surface s5 passes a beam coming from correcting plate 710, but reflects rays coming from spherical mirror 716. That is, electromagnetic radiation conditioned by correcting plate 710 passes through transparent portion 1403 of surface s5 in monolithic glass element 712 and impinges on spherical convex mirror 716.

Monolithic glass element 712 includes surfaces s4, s5 and s6. Surface s5 of monolithic glass element 712 receives the electromagnetic radiation reflected by spherical convex mirror 716 (surface s4) and reflects this electromagnetic radiation toward a target portion of the wafer. Before impinging on the target portion of the wafer, the electromagnetic radiation traverses surface s6 of monolithic glass element. Importantly, all rays reflecting off of aspheric reflective surface s5 exit monolithic glass element 712 perpendicular to surface s6, and are therefore not refracted by surface s6. As a result, catadioptric optical system 700 is achromatic.

An example prescription for designing the optical surfaces depicted in the embodiment of FIG. 7 is set forth below in Table 3.

TABLE 3

|    | Surface type | Radius   | Thickness | Glass      |
|----|--------------|----------|-----------|------------|
| s1 |              | Infinity | 3         | SIO2       |
| s2 | Asphere 1    | 48.431   | 3.000     |            |
| s3 | Asphere 2    | 49.456   | 36.812    | SIO2       |
| s4 |              | 4.285    | -36.812   | SIO2 mirror|
| s5 | Asphere 2    | 49.456   | 38.812    | SIO2 mirror|
| s6 |              | 28.876   | 28.906    |            |

Aspheric surfaces s2 and s5 of the embodiment depicted in FIG. 7 are defined by Eq. 1 in accordance with the parameters set forth below in Table 4.

TABLE 4

|                         | Asphere 1 | Asphere 2 |
|-------------------------|-----------|-----------|
| Y Radius                | 48.43064  | 49.45648  |
| Conic Constant (K)      | 0         | -0.05983  |
| 4th Order Coefficient (A) | -0.00013 | 1.22E-09  |
| 6th Order Coefficient (B) | -3.90E-07 | -3.02E-13 |
| 8th Order Coefficient (C) | 1.88E-07 | 7.79E-16  |
| 10th Order Coefficient (D)| 4.24E-09 | -7.70E-19 |
| 12th Order Coefficient (E)| 0       | 4.54E-22  |
| 14th Order Coefficient (F)| 0       | -1.46E-25 |
| 16th Order Coefficient (G)| 0       | 2.24E-29  |
| 18th Order Coefficient (H)| 0       | -9.16E-34 |
| 20th Order Coefficient (J)| 0       | 0         |

Figure 8:
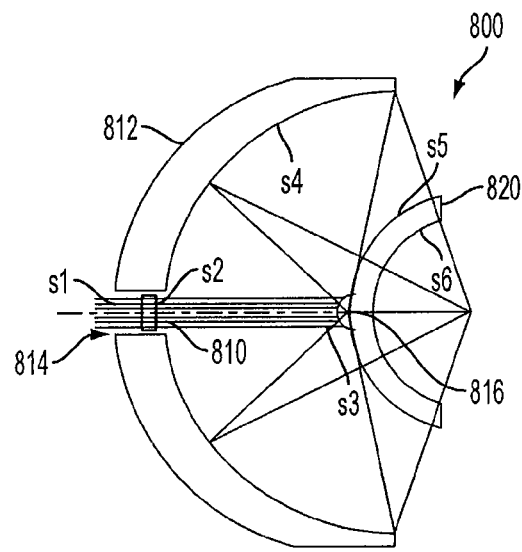

FIG. 8 depicts an example catadioptric optical system 800 in accordance with a further embodiment of the present invention. As shown in FIG. 8, catadioptric optical system 800 includes a correcting plate 810, a spherical convex mirror 816, an aspherical concave mirror 812, and a element 820.

Correcting plate 810 conditions a beam of electromagnetic radiation to correct one or more optical aberrations (such as coma). Correcting plate 810 includes an aspherical surface s1 and a surface s2. As illustrated in FIG. 8, correcting plate 810 is positioned in a hole 814 of aspherical concave mirror 812.

Spherical convex mirror 816 comprises a spherical reflective surface s3 that is positioned to reflect the electromagnetic radiation conditioned by correcting plate 810. In the embodiment depicted in FIG. 8, spherical convex mirror 816 is positioned on a surface s5 of element 820. Electromagnetic radiation conditioned by correcting plate 810 impinges on spherical convex mirror 816.

Aspherical concave mirror 812 includes aspheric reflective surface s4. Aspherical reflective surface s4 of aspherical concave mirror 812 receives the electromagnetic radiation reflected by spherical convex mirror 816 and reflects this electromagnetic radiation toward element 820 (e.g., a meniscus).

Element 820 includes a first surface s5 and a second surface s6. The electromagnetic radiation reflected by aspherical concave mirror 812 passes through element 820 perpendicular to both first surface s5 and second surface s6, and is therefore not refracted at either surface of element 820. As a result, catadioptric optical system 800 is achromatic.

An example prescription for designing the optical surfaces depicted in the embodiment of FIG. 8 is set forth below in Table 5.

TABLE 5

|    | Surface type | Radius    | Thickness | Glass  |
|----|--------------|-----------|-----------|--------|
| s1 | Asphere1     | 35.0201   | 3.423206  | SIO2   |
| s2 |              | 37.66516  | 38        |        |
| s3 |              | 3.938284  | -37.0071  | mirror |
| s4 | Asphere2     | 49.08037  | 39.65516  | mirror |
| s5 |              | 27.36549  | 5.057223  | SIO2   |
| s6 |              | 22.30041  | 21.53205  |        |

Aspheric surfaces s1 and s4 of the embodiment depicted in FIG. 8 are defined by Eq. 1 in accordance with the parameters set forth below in Table 6.

TABLE 6

|                         | Asphere 1 | Asphere 2 |
|-------------------------|-----------|-----------|
| Y Radius                | 35.0201   | 49.08037  |
| Conic Constant (K)      | 0         | -0.05525  |
| 4th Order Coefficient (A) | -0.0003 | 1.70E-09  |
| 6th Order Coefficient (B) | 3.15E-05 | -4.19E-13 |
| 8th Order Coefficient (C) | -1.10E-06 | 2.77E-16 |
| 10th Order Coefficient (D)| 0       | -4.10E-20 |
| 12th Order Coefficient (E)| 0       | 0         |
| 14th Order Coefficient (F)| 0       | 0         |
| 16th Order Coefficient (G)| 0       | 0         |
| 18th Order Coefficient (H)| 0       | 0         |
| 20th Order Coefficient (J)| 0       | 0         |

Figure 9:
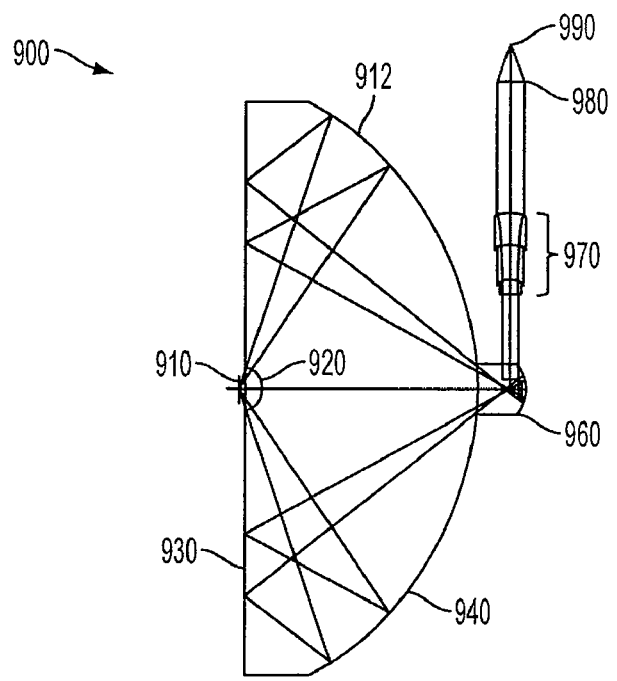

FIG. 9 depicts an illumination mode of catadioptric optical system 900 in accordance with a further embodiment of the present invention. Catadioptric optical system 900 has an illumination numerical aperture of approximately 0.95 and works in a wide spectral range from approximately 300 nanometers to 800 nanometers. The short wavelength range is limited by the transmission of $BAL_{35}Y$ glass and can be extended by using only fused silica and calcium fluoride for lens elements. Then, an even shorter wavelength range can be achieved. Catadioptric optical system 900 creates a small spot (such as, for example, about a 10 micron spot) on a wafer 910 that can be used to test wafer 910 by employing scatterometry techniques.

Catadioptric optical system 900 includes a spherical refractive surface 920, a plane reflective surface 930, an aspherical reflective surface 940, an optical element 960, a group of lenses 970, a subsidiary lens 980, and an illumination source 990 conjugate to the spot on wafer 910. Illumination source 990 provides electromagnetic radiation that propagates through subsidiary perfect lens 980 (real illuminator is not shown) and lenses 970. Lenses 970 are made of, for example, glasses $BAL_{35}Y$, $CaF_2$ and $SiO_2$ that have at least one aspheric surface. Lenses 970 function to correct aberrations (such as coma) of catadioptric optical system 900. Optical element 960 directs the electromagnetic radiation from lenses 970 to reflect off of plane reflective surface 930. The electromagnetic radiation then reflects off of aspherical reflective surface 940, passes through spherical refractive surface 920, and is focused on wafer 910. Importantly, the electromagnetic radiation traverses spherical refractive surface 920 in a direction that is substantially perpendicular to surface 920. As a result, catadioptric optical system 900 is achromatic.

As mentioned above, catadioptric optical system 900 can be used to test or sense features of wafer 910. In the sensing mode, catadioptric optical system 900 works as a high numerical aperture Fourier objective, wherein electromagnetic radiation propagates in the opposite direction of that shown in FIG. 9. Specifically, electromagnetic radiation will diffract off the surface of wafer 910, traverse through catadioptric optical system 900, and impinge upon a CCD located in a plane conjugate with the back focal plane of catadioptric optical system (i.e., the pupil plane). Light spots located at different points on the CCD correspond to beams of electromagnetic radiation diffracted at different angles from the surface of wafer 910. Using known scatterometry techniques, these light spots can be used to analyze features of wafer 910 (such as CD and overlay).

Figure 10:
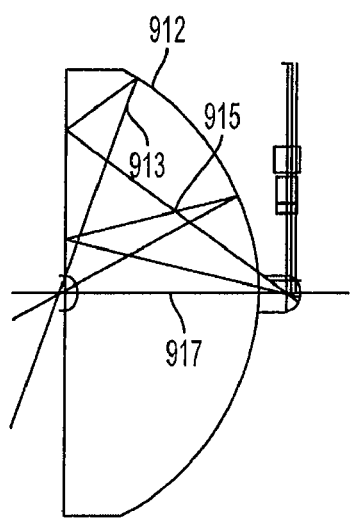
FIG. 10 depicts rays traversing the catadioptric optical system of FIG. 9.

For example, FIG. 10 depicts three diffracted beams 913, 915, and 917 (corresponding to diffracted rays at about 0, 30, and 72 degrees from the surface of wafer 910) propagating through catadioptric optical system 900 in the sensing mode. The diffracted beams create a Fourier pattern in the pupil plane of catadioptric optical system 900.

Figure 11:
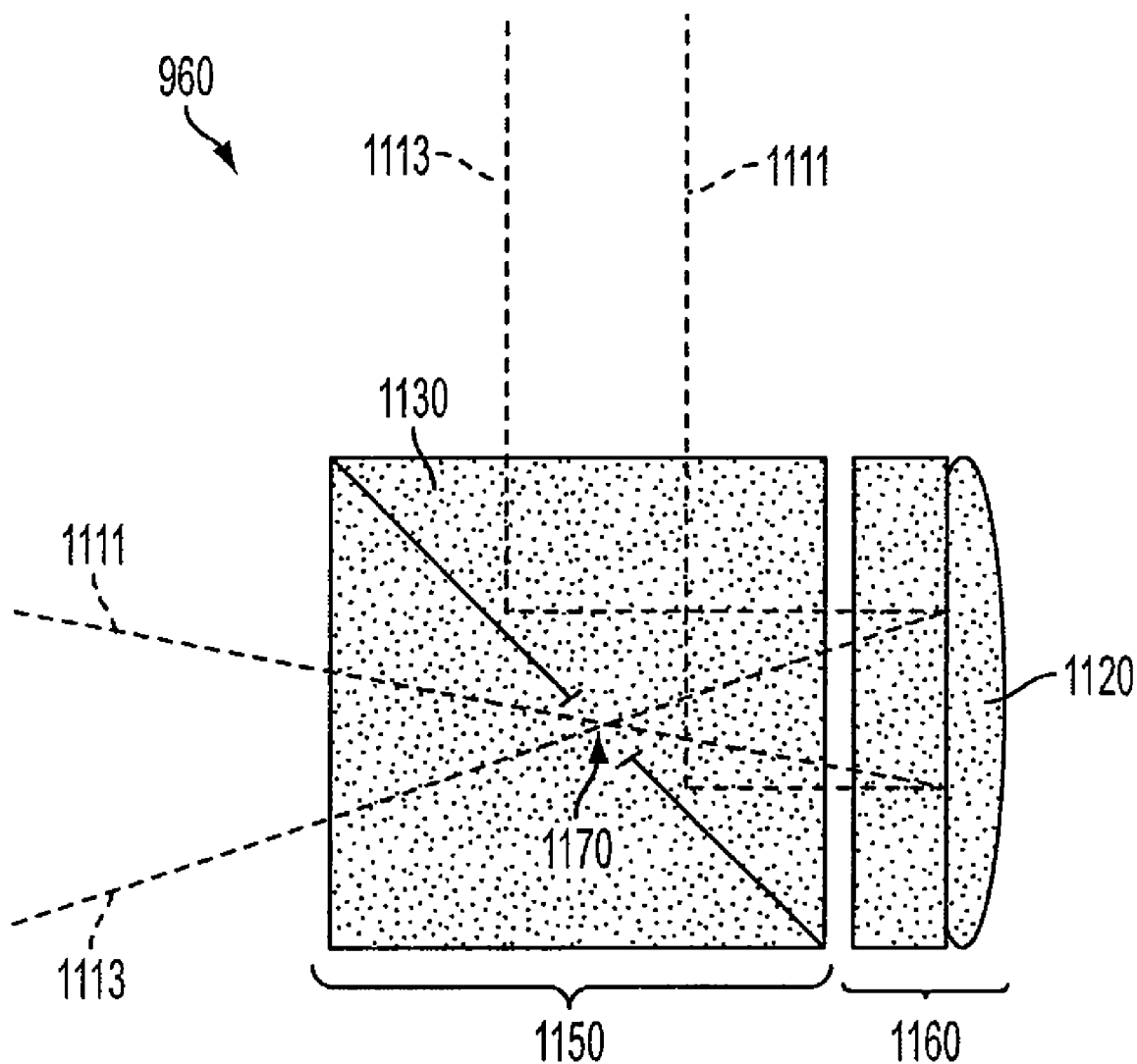
FIG. 11 depicts details of a beam splitter included in the catadioptric optical system of FIG. 9.

FIG. 11 depicts an embodiment of optical element 960. In this embodiment, optical element 960 includes a reflective hypotenuse 1130 and an aspherical reflective surface 1120. The reflection coating on hypotenuse 1130 includes a hole 1170 to transmit electromagnetic radiation refracted from the surface of wafer 910 and to reflect collimated electromagnetic radiation from illumination source 990, as shown in FIG. 9. For example, FIG. 11 depicts two example rays 1111 and 1113 reflecting off reflective hypotenuse 1130 and aspherical reflective surface 1120, and passing through hole 1170.

Referring again to FIG. 9 and continuing reference to FIG. 11, a focal lens group 970 (FIG. 9) and aspheric reflective surface 1120 are used to create an intermediate image of illumination source 990 on the hypotenuse of optical element 960 (at the location of hole 1170). Aspherical mirror 940, plane mirror 930, and refractive spherical surface 920 collectively create a final illumination spot on wafer 910.

As shown in FIG. 9, aspherical mirror 940, plane mirror 930, and refractive spherical surface 920 can be made from a monolithic glass optical element 912. Monolithic glass optical element 912 can be fabricated from a glass (such as, for example, $SiO_2$) that transmits in a spectral range from approximately 200 nanometers to 1000 nanometers.

Figure 15:
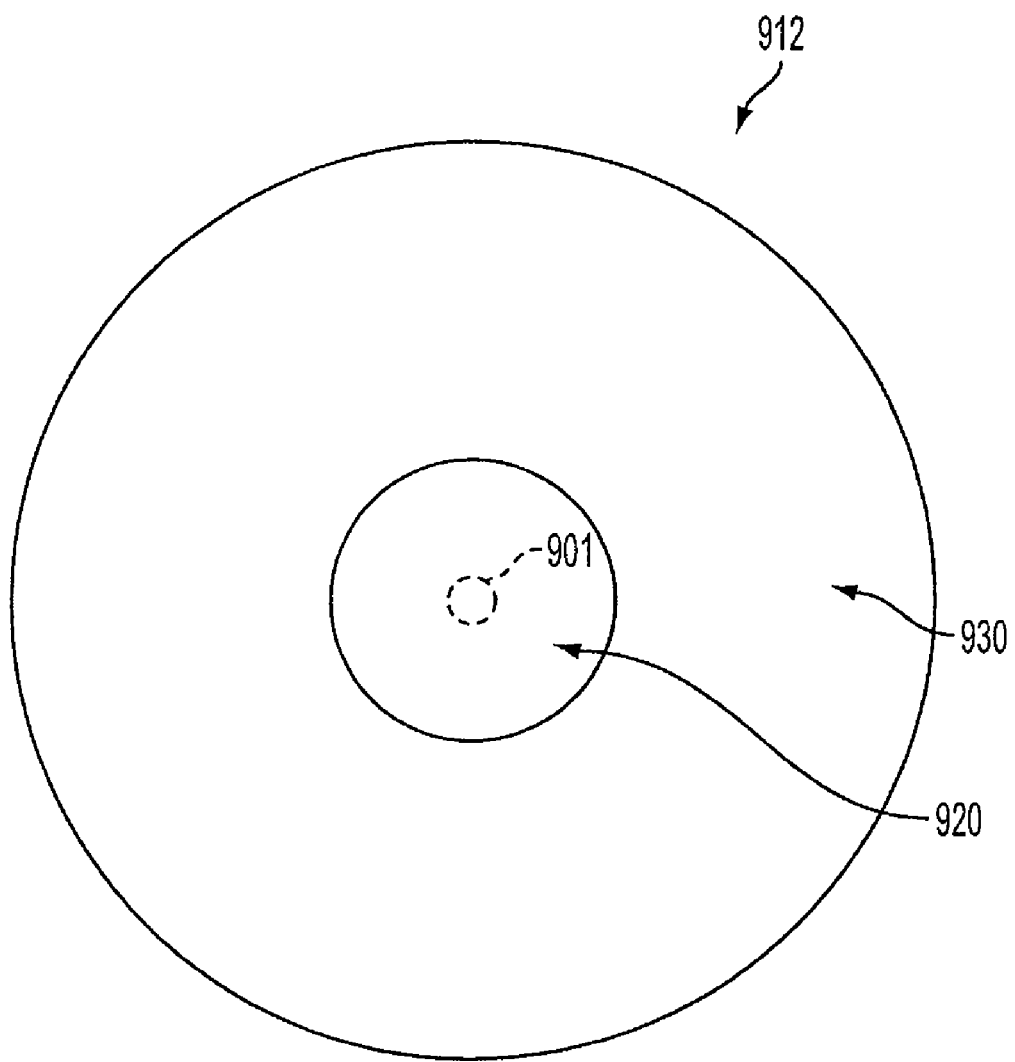
FIG. 15 depicts a plan view of a monolithic glass element included in the catadioptric optical system of FIG. 9.

For example, FIG. 15 depicts a plane view of a portion of monolithic glass optical element 912 comprising plane mirror 930 and refractive spherical surface 920. In this example, plane mirror 930 comprises an annulus with refractive spherical surface 920 positioned in the center of the annulus. Monolithic glass optical element 912 is oriented to cause an illumination spot 901 on wafer 910 to be concentric with plane mirror 930 and refractive spherical surface 920.

Optical element 960 can be fabricated from the same material as monolithic glass element 912 and assembled by optically contacting it with monolithic glass element 912. Optical element 960 can be fabricated as a monolithic glass element or as assembly of two elements, comprising a first element 1150 and a second element 1160, as depicted in FIG. 11. In one example, if optical element 960 is assembled from first element 1150 and second element 1160, it can compensate for aberration due to fabrication defects (by moving first element 1150 relative to second element 1160).

An example prescription for designing the optical surfaces of catadioptric optical system 900 is set forth below in Table 7.

TABLE 7

| | Surface type | Radius | Thickness | Glass |
|---|---|---|---|---|
| s1 | | Infinity | 3.5 | |
| s2 | | −3.500 | 32.587 | SIO2 |
| s3 | Asphere 1 | −48.765 | −35.087 | SIO2 mirror |
| s4 | | Infinity | 35.087 | SIO2 mirror |
| s5 | | Infinity | 5.000 | SIO2 |
| s6 | | Infinity | 2.500 | SIO2 |
| s7 | Asphere 2 | −5.000 | −2.500 | SIO2 mirror |
| s8 | | Infinity | 2.500 | SIO2 mirror |
| s9 | | Infinity | 12.756 | |
| s10 | | −10.544 | 2.000 | BAL35Y |
| s11 | | 43.784 | 0.100 | |
| s12 | Asphere 3 | 137.905 | 5.000 | CAF2 |
| s13 | | −10.967 | 0.973 | |
| s14 | | −9.745 | 5.000 | SIO2 |
| s15 | | −9.210 | 0.101 | |
| s16 | | Infinity | 6.02047 | |

Aspheric surfaces s3 and s7, and s12 of catadioptric optical system 900 are defined by Eq. 1 in accordance with the parameters set forth below in Table 8.

TABLE 8

| | Asphere 1 | Asphere 2 | Asphere 3 |
|---|---|---|---|
| Y Radius | −48.7652 | −5 | 137.9052 |
| Conic Constant (K) | −0.12342 | −0.35269 | −2E+07 |
| 4th Order Coefficient (A) | 0 | −0.00015 | −0.00176 |
| 6th Order Coefficient (B) | 0 | 4.95E−05 | −0.00543 |
| 8th Order Coefficient (C) | 0 | −8.08E−06 | 0.004039 |
| 10th Order Coefficient (D) | 0 | 1.25E−06 | −0.00162 |

Figure 12:
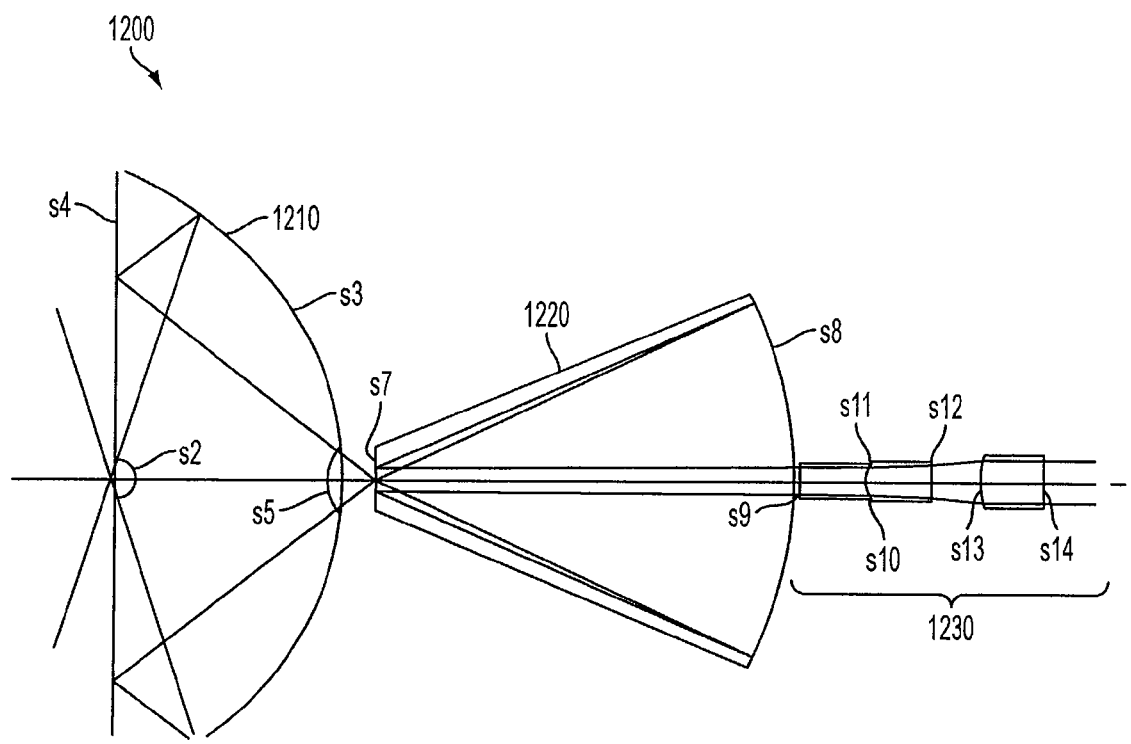
FIG. 12 depicts a catadioptric optical system that transforms from a very low numerical aperture to a very high numerical aperture.

FIG. 12 depicts an example catadioptric optical system 1200 in accordance with a further embodiment of the present invention. Catadioptric optical system 1200 includes a first monolithic glass element 1210, a second monolithic glass element 1220, and a refractive lens group 1230 cascaded together. Monolithic glass element 1210 transitions from a numerical aperture of approximately 0.95 to numerical aperture of approximately 0.4 (and back). Cascading monolithic glass elements 1210 and 1220 transitions from a numerical aperture of approximately 0.95 to a numerical aperture of approximately 0.02.

First monolithic glass element 1210 includes a refractive surface s2, an aspherical reflective surface s3, a plane reflective surface s4, and a refractive surface s5. As illustrated in FIG. 12, refractive surface s2 is positioned in the center of plane reflective surface s4, and refractive surface s5 is positioned in the center of aspherical reflective surface s3.

Second monolithic glass element 1220 includes a reflective surface s7 and a reflective surface s8. Reflective surfaces s7 and s8 each include a central, transparent portion.

Refractive lens group 1230 includes optical surfaces s9, s10, s11, s12, s13, and s14, which are positioned and shaped to correct one or more aberrations (such as coma).

This optical design functions similar to the designs depicted in FIGS. 9 and 10, but has just one aspheric surface (aspherical reflective surface s3 of first monolithic glass element 1210) and a wider spectral range (200 to 1000 nanometers).

For example, electromagnetic radiations enters catadioptric optical system 1200 through refractive lens group 1230. The electromagnetic radiation passes through refractive lens group 1230, and then through the central, transparent portion of reflective surface s8.

The electromagnetic radiation passing through the central, transparent portion of reflective surface s8 is reflected by reflective surface s7 and then received by reflective surface s8. Reflective surface s8 focuses the electromagnetic radiation into a focused spot of electromagnetic radiation that passes through the central, transparent portion of reflective surface s7. That is, second monolithic glass element 1220 is configured to provide a focused spot of electromagnetic radiation.

Refractive surface s5 of first monolithic glass element 1210 is positioned to be concentric with the focused spot of electromagnetic radiation from second monolithic glass element 1220. Consequently, electromagnetic radiation from second monolithic glass element 1220 enters monolithic glass element 1210 substantially perpendicularly to refractive surface s5. Reflective surface s4 receives this electromagnetic radiation and reflects it toward aspherical reflective surface s3. Aspherical reflective surface s3 focuses the electromagnetic radiation onto a focused spot on a wafer (not specifically shown in FIG. 12). Refractive surface s2 is positioned to be concentric to the focused spot on the wafer, thereby causing the electromagnetic radiation to exit first monolithic glass element 1210 substantially perpendicular to refractive surface s2.

Because electromagnetic radiation enters and exits first monolithic glass element 1210 substantially perpendicularly to refractive surfaces s5 and s2, catadioptric optical system is substantially achromatic—having a spectral range of approximately 200 to 1000 nanometers.

An example prescription for designing the optical surfaces of catadioptric optical system 1200 is set forth below in Table 9.

TABLE 9

| Surface type | | Radius | Thickness | Glass |
|---|---|---|---|---|
| s1 | | Infinity | 3.500 | |
| s2 | | −3.500 | 32.592 | SIO2 |
| s3 | Asphere | −48.779 | −35.100 | SIO2 mirror |
| s4 | | Infinity | 32.592 | SIO2 mirror |
| s5 | | 7.222 | 7.690 | |
| s7 | | −8.826 | 65.113 | SIO2 |
| s8 | | −67.336 | −65.113 | SIO2 mirror |
| s7 | | −8.826 | 65.113 | SIO2 mirror |
| s8 | | −67.336 | 1.140 | |
| s9 | | −32.636 | 10.000 | SIO2 |
| s10 | | 5.830 | 0.221 | |
| s11 | | 7.575 | 10.000 | CAF2 |
| s12 | | −3630.481 | 7.832 | |

TABLE 9-continued

| Surface type | Radius | Thickness | Glass |
|---|---|---|---|
| s13 | 22.500 | 10.000 | SIO2 |
| s14 | −258.120 | 32.865 | |

Aspheric surfaces s3 of catadioptric optical system 1200 is defined by Eq. 1 in accordance with the parameters set forth below in Table 10.

TABLE 10

| | Asphere |
|---|---|
| Y Radius | −48.7787 |
| Conic Constant (K) | −0.12342 |
| 4th Order Coefficient (A) | −1.61E−09 |
| 6th Order Coefficient (B) | 9.09E−13 |
| 8th Order Coefficient (C) | −1.68E−15 |
| 10th Order Coefficient (D) | 9.65E−19 |
| 12th Order Coefficient (E) | −2.76E−22 |

IV. Conclusion

Catadioptric optical systems for scatterometer have been described. While various embodiments of the present invention have been described above, it should be understood that they have been presented by way of example only, and not limitation. It will be apparent to persons skilled in the relevant art that various changes in form and detail can be made therein without departing from the spirit and scope of the invention.

A person skilled in the relevant art(s) can modify and re-optimize the above-described embodiments to better comply with a fabrication process of or optics included in the sensing and the alignment branches. For example, convex spherical mirrors 616, 716, and 816 (of FIGS. 6, 7, and 8, respectively) can be replaced by concave or aspherical mirrors having the same focus position. Aspheric correction plates 610, 710, and 810 can be replaced by groups of spherical lenses that will generate the same wavefronts as the aspheric plates described above, but such spherical lenses are easier to fabricate. These, and other modifications, of the above-described embodiments will become apparent to a person skilled in the relevant art(s), and are intended to be within the spirit and scope of the present invention.

Furthermore, it is to be appreciated that the Detailed Description section, and not the Abstract section, is intended to be used to interpret the claims. The Abstract section may set forth one or more but not all exemplary embodiments of the present invention as contemplated by the inventor(s), and thus, are not intended to limit the present invention and the appended claims in any way.

Thus, the breadth and scope of the present invention should not be limited by any of the above-described exemplary embodiments, but should be defined only in accordance with the following claims and their equivalents.

What is claimed is:

1. A catadioptric system, comprising:
a correcting plate configured to condition electromagnetic radiation to correct at least one aberration; and
an optical system configured to reflect a first portion of the conditioned electromagnetic radiation, to refract a second portion of the conditioned electromagnetic radiation, and to focus the reflected first portion of the conditioned electromagnetic radiation onto a target portion of a substrate, wherein the first portion of the electromagnetic radiation is not refracted by an optical element, thereby allowing the catadioptric optical system to operate in a broad spectral range.

2. The catadioptric system of claim 1, wherein the optical system comprises:
a first reflective surface configured to perform the reflecting of the first portion; and
a second reflective surface configured to perform the focusing of the second portion.

3. The catadioptric system of claim 2, wherein the first reflective surface comprises a convex reflective surface.

4. The catadioptric system of claim 2, wherein the second reflective surface is a surface of a monolithic glass element.

5. The catadioptric system of claim 4, wherein the first reflective surface is positioned on a second surface of the monolithic glass element.

6. The catadioptric system of claim 2, wherein the first reflective surface is positioned between the second reflective surface and the substrate.

7. The catadioptric system of claim 6, wherein the first reflective surface is positioned on mechanical supports.

8. The catadioptric system of claim 6, wherein the first reflective surface is positioned on a meniscus.

9. The catadioptric system of claim 6, wherein the second reflective surface is positioned between the correcting plate and the first reflective surface, and the second reflective surface comprises a hole through which the electromagnetic radiation conditioned by the correcting plate passes.

10. The catadioptric system of claim 2, wherein the second reflective surface comprises a concave aspheric reflective surface.

11. The catadioptric system of claim 1, wherein the catadioptric system is included in both a sensing branch and an alignment branch of a scatterometer.

12. The catadioptric system of claim 1, wherein the correcting plate comprises an aspherical surface.

* * * * *